United States Patent
Honma et al.

(10) Patent No.: US 7,351,786 B2
(45) Date of Patent: Apr. 1, 2008

(54) POLYHYDROXYALKANOATE CONTAINING UNIT HAVING CYCLOHEXYL STRUCTURE AT SIDE CHAIN, PRODUCTION PROCESS THEREFOR, AND BINDER RESIN CONTAINING POLYHYDROXYALKANOATE

(75) Inventors: Tsutomu Honma, Kanagawa (JP); Tetsuya Yano, Kanagawa (JP); Shinya Kozaki, Tokyo (JP)

(73) Assignee: Canon Kabushiki Kaisha, Ohta-ku, Tokyo (JP)

( * ) Notice: Subject to any disclaimer, the term of this patent is extended or adjusted under 35 U.S.C. 154(b) by 231 days.

(21) Appl. No.: 10/692,206

(22) Filed: Oct. 22, 2003

(65) Prior Publication Data
US 2004/0143087 A1   Jul. 22, 2004

(30) Foreign Application Priority Data
Oct. 24, 2002   (JP) .............................. 2002-309635

(51) Int. Cl.
*C08G 63/06*      (2006.01)
*C00G 63/137*     (2006.01)

(52) U.S. Cl. .................. 528/361; 435/128; 435/135; 528/176; 528/193; 528/271; 528/272; 528/354; 528/363

(58) Field of Classification Search ................ 528/271, 528/272, 354, 361, 176, 193, 363, 364; 430/107, 430/110; 435/135, 128
See application file for complete search history.

(56) References Cited

U.S. PATENT DOCUMENTS

| | | | |
|---|---|---|---|
| 5,004,664 A | | 4/1991 | Fuller et al. |
| 6,521,429 B2 * | | 2/2003 | Honma et al. .............. 435/135 |
| 6,649,380 B1 * | | 11/2003 | Yano et al. .................. 435/135 |
| 6,858,367 B2 * | | 2/2005 | Yano et al. .................. 430/127 |
| 6,916,861 B2 * | | 7/2005 | Nomoto et al. ............. 523/160 |
| 7,045,321 B2 * | | 5/2006 | Imamura et al. ............ 435/128 |
| 7,056,708 B2 * | | 6/2006 | Kenmoku et al. .......... 435/130 |
| 7,153,622 B2 * | | 12/2006 | Honma et al. .............. 430/105 |

FOREIGN PATENT DOCUMENTS

| | | |
|---|---|---|
| JP | 6-289644 | 10/1994 |
| JP | 7-120975 | 5/1995 |
| JP | 8-262796 A | 10/1996 |
| JP | 9-274335 A | 10/1997 |
| JP | 2002-80571 A | 3/2002 |

\* cited by examiner

*Primary Examiner*—Herbert J. Lilling
(74) *Attorney, Agent, or Firm*—Morgan & Finnegan, L.L.P.

(57) ABSTRACT

Disclosed are a polyhydroxyalkanoate, containing in a polymer molecule thereof a monomer unit represented by the following general formula (1):

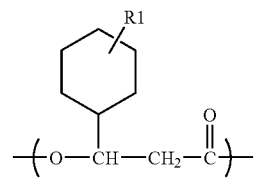

(1)

(wherein R1 represents a substituent to a cyclohexyl group, where R1 is a H atom, a CN group, a $NO_2$ group, a halogen atom, a $CH_3$ group, a $C_2H_5$ group, a $C_3H_7$ group, a $CF_3$ group, a $C_2F_5$ group, or a $C_3F_7$ group; and if there are two or more monomer units, R1 may be different from every monomer unit), and a binder resin using the polyhydroxyalkanoate. The binder resin is biodegradable, so that the binder resin is more responsible for the conservation of natural environment or the like. Also, the binder resin facilitates deinking in the deinking process using an alkali, so that the binder resin accelerates recycling of used copying paper. Furthermore, the binder resin satisfies the desired characteristics of a toner for developing an electrostatic charge image.

4 Claims, 9 Drawing Sheets

POLYHYDROXYALKANOATE CONTAINING UNIT HAVING CYCLOHEXYL STRUCTURE AT SIDE CHAIN, PRODUCTION PROCESS THEREFOR, AND BINDER RESIN CONTAINING POLYHYDROXYALKANOATE

BACKGROUND OF THE INVENTION

1. Field of the Invention

The present invention relates to a polyhydroxyalkanoate (hereinafter abbreviated as "PHA") containing a novel structural unit and a production process for the same. For instance, the present invention relates to a novel PHA that contains a monomer unit having a cyclohexyl structure at its side chain, and a production process for the PHA using an alkanoic acid as a raw material and also using a microorganism having an ability to produce and accumulate PHA in the microbial cell.

Furthermore, the present invention relates to a binder resin that can be used for an electrostatic charge image-developing toner, an electrostatic charge image-developing toner, and an image-forming method and an image-forming apparatus using the toner. For instance, the present invention relates to a binder resin, an electrostatic charge image-developing toner, an image-forming method, and an image-forming apparatus, which are used in electrophotography, electrostatic recording, and electrostatic printing by a copying machine, a printer, a facsimile machine, and so on where a toner image is formed on a latent-image bearing member (hereinafter, also simply referred to as an image bearing member) and is then transferred to a transferring material to form an image thereon. More concretely, the present invention relates to a binder resin having biodegradability so that the binder resin can be easily subjected to a waste treatment, and excellent fixing ability (low-temperature fixing ability, fixing temperature, and offset resistance) and blocking resistance, and also having a hydrolyzing ability for allowing a presently available deinking system to be directly used for the binder resin so that the binder resin can be easily deinked, and an electrostatic charge image-developing toner that contains the binder resin, and an image-forming method and an image-forming apparatus using the toner.

2. Related Background Art

Conventionally, many electrophotographic methods have been known in the art. Typically, each of the electrophotographic methods includes: forming an electric latent image on an image bearing member (a photosensitive body) by one of various kinds of means using a photoconductive material; developing the latent image with a toner to generate a visualized image; transferring a toner image to a transferring material such as a sheet of paper as needed; and fixing the toner image on the transferring material by means of, for example, heat and/or pressure to obtain a duplicate. As a method for visualizing the electric latent image, a cascade developing method, a magnetic blush developing method, a press developing method, and so on are known in the art. Furthermore, there is also known a method using a rotary developing sleeve having a magnetic toner placed thereon and having a magnetic pole arranged on the center of the developing sleeve to allow the magnetic toner to fly from the developing sleeve to a photosensitive body in the presence of a magnetic field.

As a developing system to be used for the development of an electrostatic latent image, there are two systems known in the art. The two systems are a two-component developing system using a two-component developer constructed of both a toner and a carrier and a mono-component developing system using a mono-component developer constructed only of a toner without the use of a carrier.

Here, a colored fine particle generally described as a toner includes a binder resin and a colorant as essential ingredients and includes a magnetic powder or the like as needed. By the way, the binder resin occupies most of the toner, so that physical properties of the toner can be extensively influenced by physical properties of the binder resin. For example, there is the need of providing the binder resin with delicate hardness and thermal melting characteristics. In addition, a toner obtained by pulverizing and classifying a binder resin where a coloring agent or the like is dispersed is requested to show good flowability without causing fine powders as a result of mechanical impacts by agitation in a developing device and without making the toner to be agglutinated. Furthermore, at the time of fixing, the toner should be promptly melted at low temperatures, and also at the time of melting, the melted toner should be of agglutinative. In other words, the physical properties of the toner can be controlled by controlling the physical properties of the binder resin.

Conventionally, as the binder resin, a styrene/acrylic ester copolymer, a polyester resin, an epoxy resin, an olefin resin, or the like has been used. Among them, the polyester resin is widely used as a toner resin for heat-roll fixation mainly because the toner has advantages in that the toner shows good dispersibility to a toner additive such as carbon black and good wettability to transfer paper when the resin is melted and also shows an excellent fixing ability.

In recent years, from the viewpoint of environmental protection, recycling of resources, a reduction in waste, an improvement in safety of waste, and so on have been considered on a worldwide basis. Those challenges are also concerned in the field of electrophotography without exception. That is, with the wide spread of copying machines and printers, the quantity of disposals including toners fixed on paper, waste toners after use, and printed sheets of paper is increasing every year. Typically, the conventional toner is hardly degradable because the toner is constructed of structural components respectively made of stable artificial compounds. Thus, the toner may remain in various environments including soil and water for a long period. Furthermore, for the recycling of resources, one of the important tasks is to recycle and reutilize plain paper. However, the conventional binder resins, notably styrene-based resins, are hardly deinked with alkali hydrolysis which is a problem in recycling plain paper. In addition, from the standpoint of maintenance of the earth environment or an influence on the human body, the safety of waste is also an important problem.

Under such a circumstance, persons skilled in the art have pursued the development of resins harmless to the human body and biodegradable with the action of microorganisms, i.e., biodegradable resins. There is described that many microorganisms produce biodegradable resins having polyester structures (hereinafter, referred to as polyhydroxyalkanoates, abbreviated as "PHA's") and accumulate the resins in the microbial bodies, respectively. It is known that such PHA's may have various kinds of compositions and structures depending on the species of microorganisms to be used for the production, the compositions of media, the conditions for culturing these microorganisms, and so on. Heretofore, from the viewpoint of improving the physical properties, studies have been mainly conducted on regulations of compositions and structures of PHA's to be produced. In the field of biomedical materials, there are already considerable results about the use of such biodegradable resins. In addition, in the field of agriculture, the resins are put into practical applications including multi-files, gardening materials, extended-release pesticides, and fertilizers. Furthermore, in the field of leisure, the biodegradable resins are used for fishing lines, fishing articles, golf articles, and so on. In addition, the resins are practically used as packing materials of daily necessities such as containers of livingwares. However, considering the wide applications of the resins as plastic materials, the physical properties of the respective resins are still insufficient under present circumstances. It is important to consider improvements in physical properties of the PHA's more widely for further improving their application ranges. Therefore, further development of or searches for PHA's that contain monomer units having various structures have been indispensable.

In the field of electrophotography, furthermore, there is proposed a method using a biodegradable resin as a binder resin for realizing a toner which can be disposed without causing any environmental contamination. Japanese Patent Application Laid-Open No. H06-289644 discloses an electrophotographic toner particularly used for thermal roll fixation, which is characterized in that a binder resin contains at least a plant wax and a biodegradable resin (e.g., polyester produced by a microorganism or a natural polymeric material originated from a plant or an animal), and that the content of the plant wax in the binder resin is in the range of 5 to 50% by mass. In addition, Japanese Patent Application Laid-Open No. H08-262796 discloses an electrophotographic toner having a binder resin and a colorant, which is characterized in that the binder resin is a biodegradable resin (e.g., aliphatic polyester resin) and the colorant is a water-insoluble pigment. Furthermore, U.S. Pat. No. 5,004,664 discloses a toner containing, as its composition, poly-3-hydroxybutyric acid, poly-3-valeric acid, or a copolymer, or a blend thereof. In those technologies, the binder resins are biodegradable, so the toners can be surely decomposed in soil when the toners are embedded in the soil. However, there are some problems with respect to essential functions of the binder resin in each of the above toners. For instance, the toner is less durable, and also the binder resin is highly hygroscopic and its electrostatic property is instable. Specifically, poly-3-hydroxybutyric acid is a hard and brittle material having a melting point of 180° C., a crystallinity of 50-70%, a Young's modulus of 3.5 GPa, and an elongation at break of 5%. Therefore, such a material is inadequate to be provided as a binder resin of the toner in practice.

In addition, there is proposed a toner mainly composed of polylactate aliphatic polyester, which has biodegradability and is efficiently decomposed in alkali hydrolysis and useful for recycling the used paper. Japanese Patent Application Laid-Open No. H07-120975 proposes a method for making a lactate homopolymer into a toner. In this document, a polylactic acid prepared by a ring-opening polymerization method is provided as a representative example of the homopolymer.

In the ring-opening polymerization method, lactic acid is oligomerized by a dehydration reaction at first, and the resulting oligomer is depolymerized to make the lactic acid into a lactide (a cyclic dimer), followed by subjecting the lactide to further ring-opening polymerization. Because the method follows such a complicated process, the resulting polylactic acid is too expensive to be used as a toner resin.

In addition, the ring-opening polymerization is of a cationic type, so that the polymerization requires making a solvent to be employed anhydrous, removable of ionic species to be provided as polymerization terminators, and so on. As a result, the ring-opening polymerization leads to poor producibility, and the monomer species that can be used for the production of polyester are limited to cyclic esters. Thus, it is difficult to provide the binder resin with physical properties desired for the toner resin. In addition, it is also difficult to prepare a copolymer with any of various monomers for controlling a balance between the degradability and the physical property. In this regard, cheap and degradable polyester the physical properties of which can be easily controlled has been demanded in the art. Additionally, when a polylactic acid is directly prepared as a toner, there are problems in storage stability and offset resistance of the toner. Thus, such a toner is not yet in the actual use.

Furthermore, Japanese Patent Application Laid-Open No. H09-274335 discloses a toner for electrostatic charge image development, which is characterized by containing: a polyester resin obtained by a dehydrating polycondensation reaction of a composition that contains lactic acid and oxycarboxylic acid having three or more functional groups; and a colorant. In this document, however, the polyester resin is prepared by the dehydrating polycondensation reaction between an alcohol group in the lactic acid and a carboxylic acid group in the oxycarboxylic acid, so that the molecular weight of the resulting resin may be higher than the desired one. Thus, the higher molecular weight is expected to lead to a decrease in biodegradability of the resin. Furthermore, as is the case with Japanese Patent Application Laid-Open No. H07-120975, there are problems in storage stability and offset resistance of the toner.

Moreover, a polycaprolactone, which is a typical single polymer of hydroxycarboxylic acid, has a low melting point and a low glass transition point, and is excellent in compatibility with various kinds of resins. However, the polycaprolactone has a melting point as low as 60° C., so that the polycaprolactone cannot be suitable for a binder resin when the polycaprolactone is used alone. In addition, polylactic acid has a high glass transition point (60° C.), and also polylactic acid having a crystalline form is a thermoplastic macromolecule having a high melting point (about 180° C.). However, as described above, the polylactic acid is not yet in the actual use as a binder resin. Furthermore, the conventional toner resin made of a biodegradable polyester shows poor grindability in general. Thus, it is difficult to use such a toner resin a binder resin that accounts for 90% of a toner having a particle size of about 10 μm. Considering the practical use of toner as a binder resin, improvements in the physical properties of the toner have been strongly demanded.

Incidentally, like the conventional plastic material, the PHA described above can be used for the production of various products by melt-processing or the like. In addition, the PHA has an advantage of being completely decomposed by microorganisms in the nature. In other words, there is no possibility that the remaining PHA pollutes the natural environment as in the case with many synthetic macromolecular compounds known in the art. In addition, the PHA is excellent in biocompatibility, so that application of the PHA to a medical soft material or the like is also expected.

As described above, it has been known that the microbial produced PHA's can have various compositions and structures depending on the species of microorganisms to be used for the production, compositions of media, conditions for culturing these microorganisms, and so on. Mainly from the view point of improving the physical properties of PHA's, the studies for adjusting the compositions and structures of the PHA's have been carried out up to now.

In particular, the biosynthesis of a PHA by polymerizing a monomer unit having a comparatively simple structure, such as 3-hydroxy-n-butyric acid (hereinafter, abbreviated as "3HB"), 3-hydroxy-n-valeric acid (hereinafter, abbreviated as "3HV"), 3-hydroxy-n-hexanoic acid (hereinafter, abbreviated as "3HHx"), or 4-hydroxy-n-butyric acid (hereinafter, abbreviated as "4HB") has been investigated, and the PHA production from various microorganisms has been reported.

Furthermore, in recent years, a PHA that is composed of a 3-hydroxyalkane acid with a medium chain length (abbreviated as "mcl") having up to 12 carbons has been under intense study. The production of mcl-PHA using a noncyclic aliphatic hydrocarbon, octanoic acid, hexanoic acid, sodium gluconate, or the like as a carbon source has been confirmed.

By the way, the PHA's synthesized in the above example are those composed of monomer units having alkyl groups at their respective side chains. In other words, therefore, those PHA's are "usual PHA's".

However, considering broader applications of PHA's, for example applications of PHA's to functional polymers, it is expected that the PHA where a substituent except an alkyl group introduced in the side chain thereof, i.e., "unusual PHA", is extremely useful. Examples of such a substituent include those having aromatic rings (such as a phenyl group, a phenoxy group, and a benzoyl group), an unsaturated hydrocarbon, an ester group, an allyl group, a cyano group, a halogenated hydrocarbon, and an epoxide. Among them, in particular, the PHA's having aromatic rings have been actively investigated in the art.

Reported as the production of a PHA containing a phenyl group or a partially substituted product thereof are, for example: production of a PHA containing 3-hydroxy-5-phenylvaleric acid as a unit using 5-phenylvaleric acid as a substrate; production of a PHA containing 3-hydroxy-5-(4'-tolyl)valeric acid as a unit using 5-(4'-tolyl)valeric acid as a substrate; and production of a PHA containing 3-hydroxy-5-(2',4'-dinitrophenyl)valeric acid and 3-hydroxy-5-(4'-nitrophenyl)valeric acid as units using 5-(2',4'-dinitrophenyl)valeric acid as a substrate. Reported as the production of a PHA containing a phenoxy group or a partially substituted product thereof are, for example: production of a PHA copolymer of 3-hydroxy-5-phenoxyvaleric acid and 3-hydroxy-9-phenoxynonanoic acid using 11-phenoxyundecanoic acid as a substrate; production of a PHA containing a 3-hydroxy-4-phenoxybutyrate unit and a 3-hydroxy-6-phenoxyhexanoate unit from 6-phenoxyhexanoic acid; production of a PHA containing a 3-hydroxy-4-phenoxybutyrate unit, a 3-hydroxy-6-phenoxyhexanoate unit, and a 3-hydroxy-8-phenoxyoctanoate unit from 8-phenoxyoctanoic acid; and production of a PHA containing a 3-hydroxy-5-phenoxyvalerate unit and a 3-hydroxy-7-phenoxyheptanoate unit from 11-phenoxyundecanoic acid. In addition, reported are a PHA homopolymer of a 3-hydroxy-5-(monofluorophenoxy)pentanoate (3H5(MFP)P) unit or a 3-hydroxy-5-(difluorophenoxy)pentanoate (3H5(DFP)P) unit and a PHA copolymer containing at least a 3H5(MFP)P unit or a 3H5(DFP)P unit. The effect thereof is that stereoregularity and repellency are given while a high melting point and excellent processability are being kept. In addition to the fluorine-group-substituted products described above, cyano-group-substituted products and nitro-group-substituted products have also been investigated. For example, reported is production of a PHA containing 3-hydroxy-p-cyanophenoxyhexanoic acid or 3-hydroxy-p-nitrophenoxyhexanoic acid as a monomer unit using octanoic acid and p-cyanophenoxyhexanoic acid or p-nitrophenoxyhexanoic acid as substrates. The PHA's described in those reports differ from a general PHA having an alkyl group in a side chain, and each of the PHA's has an aromatic ring at the side chain, which is beneficial in obtaining a polymer having physical properties derived from the aromatic ring. In addition, as an unusual PHA having a cyclohexyl group, for example, production of the PHA from cyclohexylbutyric acid or cyclohexylvaleric acid is reported.

As described above, the microbial produced PHA's may have various kinds of compositions and structures by changing species of the microorganisms to be used for the production, compositions of media, conditions for culturing these microorganisms, and so on. However, considering their applications to plastic materials, the physical properties of the PHA's are still insufficient. For extending the application scope of a microbial produced PHA, it is important to more broadly consider improvements in its physical properties. Therefore, it is indispensable to further develop and search PHA's that contain monomer units having various structures respectively, the production method thereof, and microorganisms that can effectively produce desired PHA's.

On the other hand, a PHA of a type having a side chain in which a substituent is introduced as described above (i.e., unusual PHA) can be expected to be deployed as a "functional polymer" having extremely useful functions and characteristics originating from the characteristics or the like of the introduced substituent by selecting the introduced substituent depending on the desired characteristics or the like. Therefore, it is also an important objective to develop and search such an excellent PHA with compatibility between such functionality and biodegradability, a production method thereof, and a microorganism capable of effectively producing the desired PHA.

SUMMARY OF THE INVENTION

An object of the present invention is to solve the problems with the PHA's and to provide a PHA containing a monomer unit having a cyclohexyl structure at its side chain, the PHA being useful for a device material, a medical material, a binder resin, or the like, and a method for producing the PHA by means of a microorganism.

Another object of the present invention is to solve the problems in electrophotography and to provide: a binder resin characterized in that the binder resin is biodegradable and more responsible for the conservation of natural environment and so on, that the binder resin facilitates deinking in the conventional deinking process using alkali to accelerate recycling of used copy paper, and that the binder resin complies specific characteristics required of a toner, such as carrier spent, fogging, electrostatic stability and durability, storage stability, grindability, and cost effectiveness; an electrostatic charge image-developing toner, which contains the binder resin; and an image-forming method and an image-forming apparatus using the toner.

The inventors of the present invention have strived to develop a PHA having a functional group at its side chain, the PHA being useful as a device material, a medical material, a binder resin, or the like. Thus, the inventors of the present invention have searched microorganisms having the abilities to produce various PHA's and to accumulate the PHA's in their microbial bodies, and have made extensive studies over and over to provide a production process for a desired PHA using any of such microorganisms. As a result, the inventors of the present invention have found microorganisms capable of producing a novel PHA that contains a monomer unit represented by the following general formula (1):

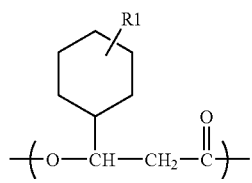

(1)

(wherein R1 represents a substituent to a cyclohexyl group, where R1 is one selected from the group consisting of a H atom, a CN group, a $NO_2$ group, a halogen atom, a $CH_3$ group, a $C_2H_5$ group, a $C_3H_7$ group, a $CF_3$ group, a $C_2F_5$ group, and a $C_3F_7$ group; and if there are two or more monomer units, R1 may be different from every monomer unit) by using an alkanoic acid represented by the following general formula (17) as a raw material and capable of accumulating the PHA in their microbial cells:

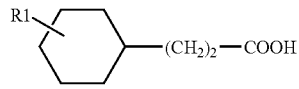

(17)

(wherein R1 represents a substituent to a cyclohexyl group, where R1 is one selected from the group consisting of a H atom, a CN group, a $NO_2$ group, a halogen atom, a $CH_3$ group, a $C_2H_5$ group, a $C_3H_7$ group, a $CF_3$ group, a $C_2F_5$ group, and a $C_3F_7$ group, each of which is corresponding to R1 in the general formula (1); and if there are two or more monomer units, R1 may be different from every monomer unit). In addition, the inventors of the present invention have found that the PHA's can be biosynthesized by culturing those microorganisms in the presence of saccharide, polypeptone, or yeast extract together with the alkanoic acids represented by the general formula (17). Furthermore, the inventors of the present invention have found that a binder resin containing a PHA having the monomer unit with a cyclohexyl structure at its side chain in the polymer molecule represented by the formula (1) has extremely excellent characteristics as a binder resin and a high level of safety with respect to the human body and the environment, and also an electrostatic charge image-developing toner containing the binder resin exerts remarkable effects when the toner is used in an image-forming apparatus having a certain developing system. Consequently, the inventors of the present invention have finally achieved the present invention.

Therefore, the present invention relates to a PHA characterized by containing in a polymer molecule thereof a monomer unit represented by the general formula (1).

Further, the present invention relates to a production process for the PHA containing in a polymer molecule thereof a monomer unit represented by the general formula (1), the method being characterized by including a step of culturing a microorganism having a PHA-producing ability in a medium containing an alkanoic acid represented by the general formula (17).

In addition, the present invention relates to a binder resin that forms a resin bulk material, characterized by containing a PHA having a monomer unit represented by the general formula (1) in its polymer molecule.

Furthermore, the present invention relates to an electrostatic charge image-developing toner, characterized by containing any one of the binder resins described above.

Further, the present invention relates to an image-forming method characterized by including the steps of: charging an electrostatic latent image bearing member by externally applying a voltage to a charging member; forming an electrostatic charge image on the charged electrostatic latent image bearing member; developing the electrostatic charge image with an electrostatic charge image-developing toner to form a toner image on the electrostatic latent image bearing member, the electrostatic charge image-developing toner being the above-described electrostatic charge image-developing toner; transferring the toner image on the electrostatic latent image bearing member to a recording medium; and thermally fixing the toner image on the recording medium.

Further, the present invention relates to an image-forming apparatus characterized by including: means for charging an electrostatic latent image bearing member by externally applying a voltage to a charging member; means for forming an electrostatic charge image on the charged electrostatic latent image bearing member; means for developing the electrostatic charge image with an electrostatic charge image-developing toner to form a toner image on the electrostatic latent image bearing member, the electrostatic charge image-developing toner being the above-described electrostatic charge image-developing toner; means for transferring the toner image on the electrostatic latent image bearing member to a recording medium; and means for thermally fixing the toner image on the recording medium.

Like the PHA of the present invention, the present invention has realized for the first time a PHA having a bulky chemical structure such as a cyclohexyl ring system directly bonded to the main chain of a polymer without through a methylene chain ($—(CH_2)_n—$). Therefore, the novel PHA and the production process therefor of the present invention are extremely useful for improving and controlling the physical properties and functionality of the PHA, and are capable of sharply expanding the application of the microbial produced PHA.

In the production process for the PHA of the present invention, a microorganism is cultured in a culture medium containing 3-cyclohexylpropionic acid as a raw material to allow the microorganism to effectively produce a novel PHA that contains the corresponding 3-hydroxy-3-cyclohexylpropionate unit. In addition, the PHA of the present invention is one useful as a functional polymer, so that the application of the PHA to each of the fields including device materials, medical materials, and binder resins can be expected.

According to the invention, the PHA containing a 3-hydroxy-3-cyclohexylpropionate unit in its polymer molecule is used as a binder resin. Thus, it becomes possible to provide a binder resin that is biodegradable and more responsible for the conservation of natural environment or the like, facilitates deinking in the deinking process using alkaline to accelerate the recycling of used copy paper, and satisfies the characteristics required of a toner, such as carrier spent, fogging, electrostatic stability and durability, storage stability, grindability, and cost effectiveness. Furthermore, it becomes possible to provide an electrostatic charge image-developing toner containing the binder resin, and an image-forming method and an image-forming apparatus using the toner.

DESCRIPTION OF THE PREFERRED EMBODIMENTS

PHA

Figure 1:
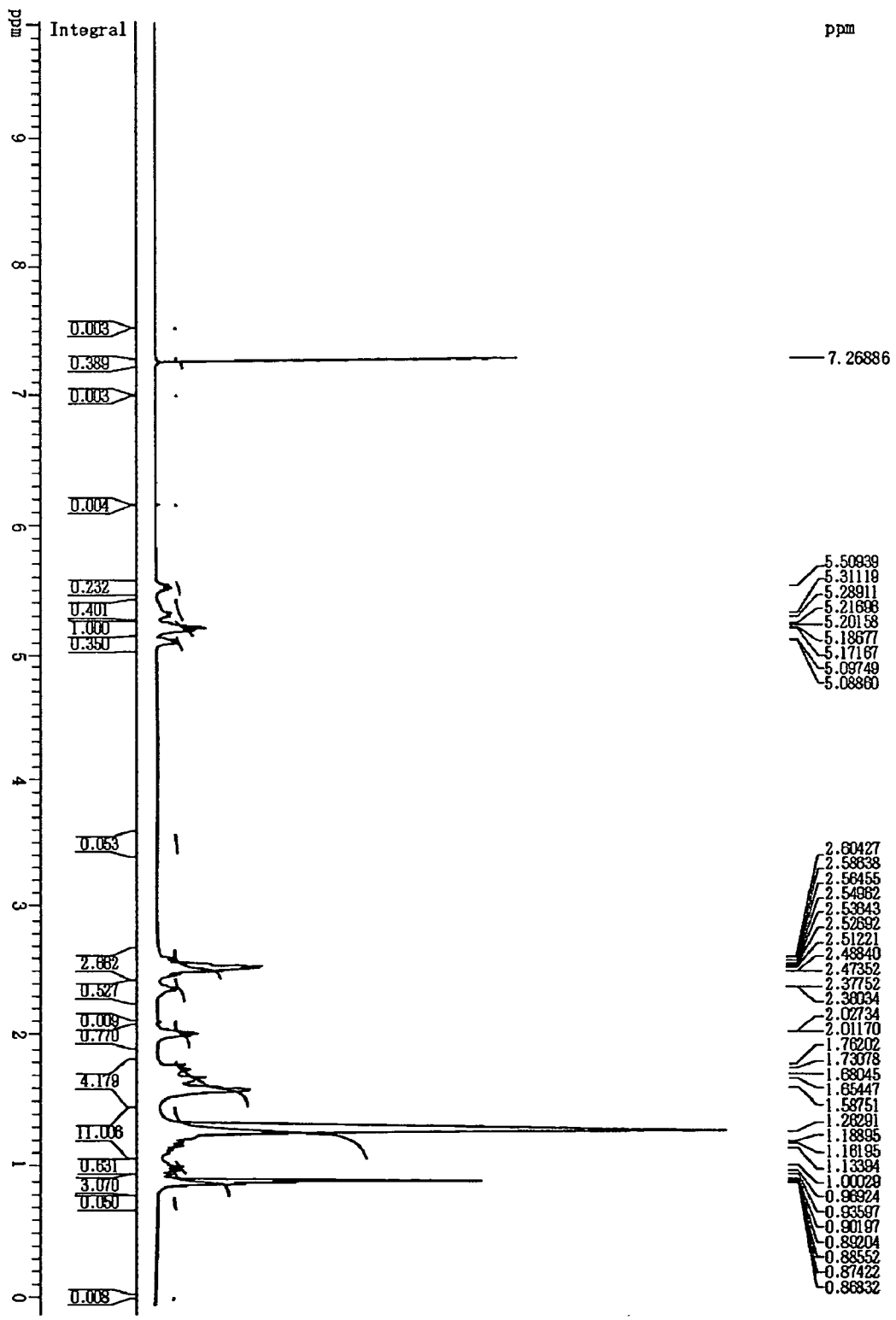
FIG. 1 is a $^1$H-MMR spectrum chart measured for a PHA obtained in Example 1.

A PHA according to the present invention contains in a polymer molecule thereof a monomer unit represented by the following general formula (1):

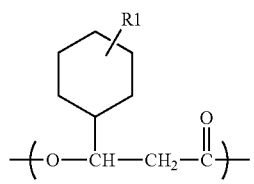

(1)

(where R1 represents a substituent to a cyclohexyl group, where R1 is one selected from the group consisting of a H atom, a CN group, a $NO_2$ group, a halogen atom, a $CH_3$ group, a $C_2H_5$ group, a $C_3H_7$ group, a $CF_3$ group, a $C_2F_5$ group, and a $C_3F_7$ group; and if there are two or more monomer units, R1 may be different from every monomer unit), the PHA being useful as a device material, a medical material, a binder resin, etc. Further, the number average molecular weight of the polymer molecule is 2,000 or more but not more than 300,000.

In the PHA of the present invention, each of all 3-hydroxyalkanoate units including the units represented by the general formula (1) has an asymmetric carbon atom at position 3 thereof, and an absolute configuration of the unit is the R configuration, so that the biodegradability of the PHA can be expressed.

In addition to the monomer unit represented by the general formula (1), if required, the PHA of the present invention may further contain any of various monomer units, which can be included in microbial produced PHA'S, in the polymer molecule. Examples of such a monomer unit include, in addition to the unit represented by the general formula (1), monomer units represented by the following general formulae (2) to (15):

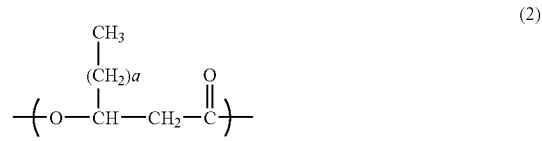

(2)

(wherein a represents an integral number of 0 to 9, and if there are two or more monomer units, a may be different from every monomer unit);

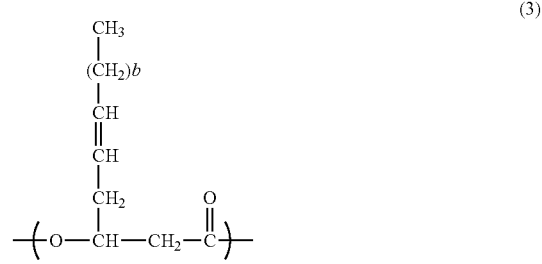

(3)

(wherein b represents either 3 or 5, and if there are two or more monomer units, b may be different from every monomer unit);

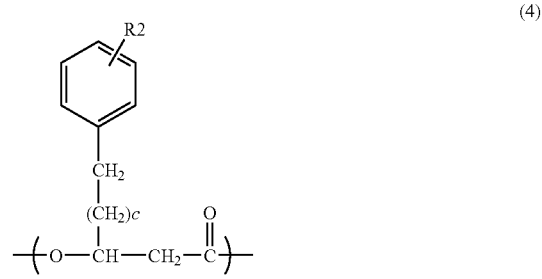

(4)

(wherein c represents an integral number of 0 to 7; and R2 represents a substituent to an aromatic ring, where R2 is one selected from the group consisting of a H atom, a halogen atom, a CN group, a $NO_2$ group, a $CH_3$ group, a $C_2H_5$ group, a $C_3H_7$ group, a $CH=CH_2$ group, COOR3 (wherein R3 represents one of a H atom, a Na atom, and a K atom), a. $CF_3$ group, a $C_2F_5$ group, and a $C_3F_7$ group; and if there are two or more monomer units, each of c, R2, and R3 may be different from every monomer unit);

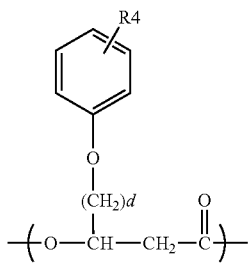

(wherein d represents an integral number of 1 to 8; and R4 represents a substituent to an aromatic ring, where R4 is one selected from the group consisting of a H atom, a halogen atom, a CN group, a $NO_2$ group, a $CH_3$ group, a $C_2H_5$ group, a $C_3H_7$ group, a $SCH_3$ group, a $CF_3$ group, a $C_2F_5$ group, and a $C_3F_7$ group; and if there are two or more monomer units, each of d and R4 may be different from every monomer unit);

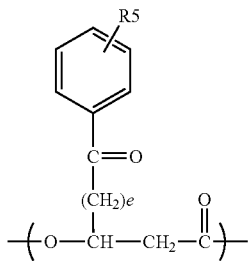

(wherein e represents an integral number of 1 to 8; and R5 represents a substituent to an aromatic ring, where R5 is one selected from the group consisting of a H atom, a halogen atom, a CN group, a $NO_2$ group, a $CH_3$ group, a $C_2H_5$ group, a $C_3H_7$ group, a $CF_3$ group, a $C_2F_5$ group, and a $C_3F_7$ group; and if there are two or more monomer units, each of e and R3 may be different from every monomer unit);

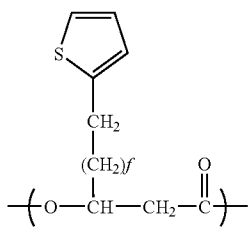

(wherein f represents an integral number of 0 to 7, and if there are two or more monomer units, f may be different from every monomer unit);

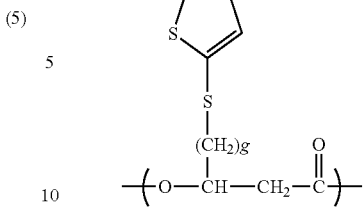

(wherein g represents an integral number of 1 to 8, and if there are two or more monomer units, g may be different from every monomer unit);

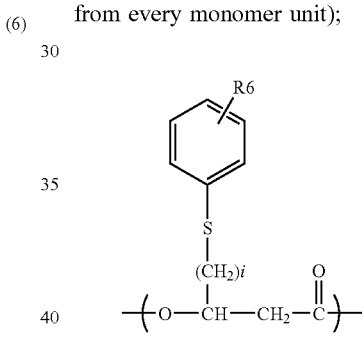

(wherein h represents an integral number of 1 to 8, and if there are two or more monomer units, h may be different from every monomer unit);

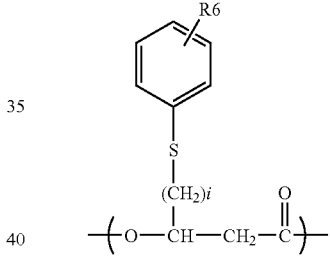

(wherein i represents an integral number of 1 to 8; and R6 represents a substituent to an aromatic ring, where R6 is one selected from the group consisting of a H atom, a halogen atom, a CN group, a $NO_2$ group, COOR7, $SO_2$R8 (wherein R7 represents one of a H atom, a Na atom, a K atom, a $CH_3$ group, and a $C_2H_5$ group; and R8 represents one of a OH group, a ONa group, a OK group, a halogen atom, a $OCH_3$ group, and a $OC_2H_5$ group), a $CH_3$ group, a $C_2H_5$ group, a $C_3H_7$ group, a $(CH_3)_2$—CH group, and a $(CH_3)_3$—C group; and if there are two or more monomer units, each of i, R6, R7, and R8 may be different from every monomer unit);

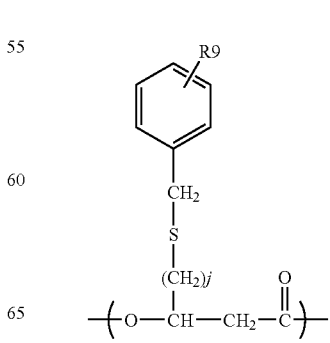

(wherein j represents an integral number of 1 to 8; and R9 represents a substituent to an aromatic ring, where R9 is one selected from the group consisting of a H atom, a halogen atom, a CN group, a NO$_2$ group, COOR10, SO$_2$R11 (wherein R10 represents one of a H atom, a Na atom, a K atom, a CH$_3$ group, and a C$_2$H$_5$ group; and R11 represents one of a OH group, a ONa group, a OK group, a halogen atom, a OCH$_3$ group, and a OC$_2$H$_5$ group), a CH$_3$ group, C$_2$H$_5$ group, C$_3$H$_7$ group, (CH$_3$)$_2$—CH group, and a (CH$_3$)$_3$—C group; and if there are two or more monomer units, each of j, R9, R10, and R11 may be different from every monomer unit);

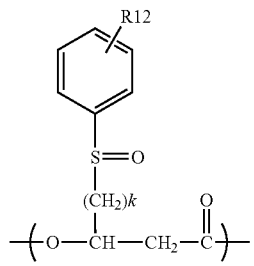

(12)

(wherein k represents an integral number of 1 to 8; and R12 represents a substituent to an aromatic ring, where R12 is one selected from the group consisting of a H atom, a halogen atom, a CN group, a NO$_2$ group, COOR13, SO$_2$R14 (wherein R13 represents one of a H atom, a Na atom, a K atom, a CH$_3$ group, and a C$_2$H$_5$ group; and R14 represents one of a OH group, a ONa group, a OK group, a halogen atom, a OCH$_3$ group, and a OC$_2$H$_5$ group), a CH$_3$ group, a C$_2$H$_5$ group, a C$_3$H$_7$ group, a (CH$_3$)$_2$—CH group, and a (CH$_3$)$_3$—C group; and if there are two or more monomer units, each of k, R12, R13, and R14 may be different from every monomer unit);

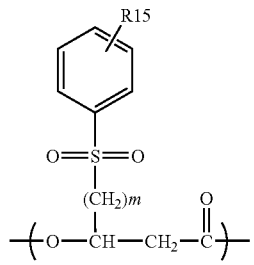

(13)

(wherein m represents an integral number of 1 to 8; and R15 represents a substituent to an aromatic ring, where R15 is one selected from the group consisting of a H atom, a halogen atom, a CN group, a NO$_2$ group, COOR16, SO$_2$R17 (wherein R16 represents one of a H atom, a Na atom, a K atom, a CH$_3$ group, and a C$_2$H$_5$ group; and R17 represents one of a OH group, a ONa group, a OK group, a halogen atom, a OCH$_3$ group, and a OC$_2$H$_5$ group), a CH$_3$ group, a C$_2$H$_5$ group, a C$_3$H$_7$ group, a (CH$_3$)$_2$—CH group, and a (CH$_3$)$_3$—C group; and if there are two or more monomer units, each of m, R15, R16, and R17 may be different from every monomer unit);

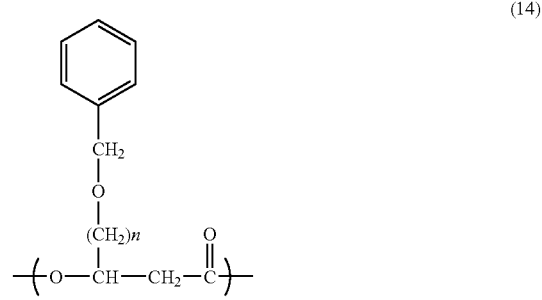

(14)

(wherein n represents an integral number of 1 to 8, and if there are two or more monomer units, n may be different from every monomer unit); and

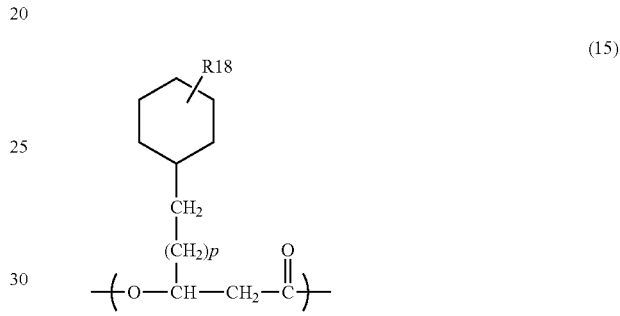

(15)

(wherein p represents an integral number of 0 to 7; and R18 represents a substituent to a cyclohexyl group, where R18 is one selected from the group consisting of a H atom, a CN group, a NO$_2$ group, a halogen atom, a CH$_3$ group, a C$_2$H$_5$ group, a C$_3$H$_7$ group, a CF$_3$ group, a C$_2$F$_5$ group, and a C$_3$F$_7$ group; and if there are two or more monomer units, each of p and R18 may be different from every monomer unit).

In addition to the monomer unit represented by the general formula (1), the introduction of at least one monomer unit represented by the general formulae (2) to (15) into the polymer molecule allows the PHA to be provided with additional functionality or allows the physical properties of the PHA to be controlled arbitrarily, and so on.

Production Process for PHA

Microorganism

In the production process for the PHA of the present invention, a microorganism to be used for the production of a PHA containing a desired monomer unit is any one of microorganisms that produce PHA's containing their corresponding 3-hydroxyalkanoate units and accumulate the PHA's in their respective cells when the microorganisms are cultured in media containing alkanoic acids represented by the following general formula (17):

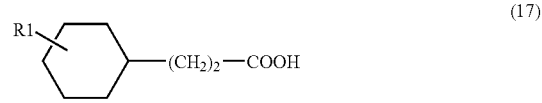

(17)

(wherein R1 represents a substituent to a cyclohexyl group, where R1 is one selected from the group consisting of a H atom, a CN group, a NO$_2$ group, a halogen atom, a CH$_3$ group, a C$_2$H$_5$ group, a C$_3$H$_7$ group, a CF$_3$ group, a C$_2$F$_5$ group, and a C$_3$F$_7$ group, each of which corresponding to R1 in the general formula (1); and if there are two or more monomer units, R1 may be different from every monomer unit). For instance, the microorganisms include those belonging to *Pseudomonas* having the PHA-producing abilities. Preferable examples of the microorganism belonging to *Pseudomonas* sp. include the following three microbial strains: a *Pseudomonas cichorii* strain YN2 (FERM BP-7375); a *Pseudomonas cichorii* strain H45 (FERM BP-7374); and a *Pseudomonas jessenii* strain P161 (FERM BP-7376). Those three microbial species were deposited within the country in advance under the name of the applicant of the present invention as a depositor, followed by being placed under the authority of another depository institution from the original deposit according to the Budapest Treaty. Then, those microbial species were respectively provided with acceptance numbers from National Institute of Bioscience and Human-Technology, Agency of Industrial Science and Technology (METI, the international depositary authority) of National Institute of Advanced Industrial Science and Technology (AIST), Ministry of Economy, Trade and Industry. Presently, the microbial species have been deposited to the National Institute of Advanced Industrial Science and Technology in METI. Furthermore, those microbial species are already described in Japanese Patent Application Laid-Open No. 2002-80571 as microbial strains having the PHA-producing abilities.

In addition to the microorganisms belonging to *Pseudomonas* sp., it is also possible to use other microorganisms that belongs to *Aeromonas* sp., *Comamonas* sp., *Burkholderia* sp., or the like, and that is capable of producing a PHA that contains a monomer unit represented by the general formula (1) with the use of an alkanoic acid represented by the general formula (17) as a raw material (a substrate).

Culture Process

The production process for a PHA of the present invention includes: culturing a microorganism having the PHA-producing ability in a medium containing an alkanoic acid represented by the general formula (17) as a raw material; and allowing the microorganism to produce a PHA containing the corresponding monomer unit represented by the general formula (1) and to accumulate the resulting PHA in its cells.

For the general culture of a microorganism, such as for preparation of a preserved microbial strain or for growth of the microorganism for ensuring the number of microbial cells and the active states thereof required for the PHA production, a medium containing components required for the growth of the microorganism to be used may be appropriately selected and used. For instance, various kinds of media including general natural media (e.g., a broth medium and a yeast extract) and synthetic media added with nutrients can be used as far as the media do not exert harmful effects on the growth and survival of microorganisms. Culture conditions including temperature, ventilation, and agitation may be suitably selected depending on the microorganism to be used.

On the other hand, when the PHA-producing microorganism is used for producing the desired PHA containing the monomer unit represented by the general formula (1), the medium may be an inorganic medium or the like that contains at least a carbon source for the growth of the microorganism in addition to the alkanoic acid represented by the general formula (17) corresponding to the monomer unit as raw materials for the PHA production. An initial content of the alkanoic acid represented by the general formula (17) and provided as a raw material may be desirably selected to be in the range of 0.01% to 1% (w/v) per medium, more preferably in the range of 0.02% to 0.2% (w/v).

Preferably, a growth substrate to be used by the microorganism for the growth thereof is separately added to the medium. Examples of the growth substrate may include a yeast extract, polypeptone, and a meat extract. Furthermore, depending on the microbial strain to be used, a suitable one can be selected from saccharide or the like in consideration of the utility of the selected one as a growth substrate.

Among those various growth substrates, preferably used as saccharides are one or more compounds selected from the group consisting of: aldoses such as glyceroaldehyde, erythrose, arabinose, xylose, glucose, galactose, mannose, and fructose; alditols such as glycerol, erythritol, and xylitol; aldonic acids such gluconic acid; uronic acids such as glucuronic acid and galacturonic acid; and disaccharides such as maltose, sucrose, and lactose.

A content of each of those growth substrates to coexist with a raw material compound may be desirably selected to be in the range of 0.1% to 5% (w/v) per medium, more preferably in the range of 0.2% to 2% (w/v) per medium.

Furthermore, for producing a PHA that further contains at least one selected from the group consisting of the monomer units represented by the general formulae (2) to (15) in its polymer molecule in addition to the monomer unit represented by the general formula (1), it is possible to employ a process for culturing a microorganism in the medium where an alkanoic acid corresponding to the desired monomer unit is additionally provided.

For instance, if it is desirable to allow a 3-hydroxy-5-cyclohexylvalerate unit represented by the general formula (18) described below to coexist with the monomer unit represented by the general formula (1) in the polymer molecule, 5-cyclohexylvalerate represented by the general formula (19) described below may be additionally provided as an alkanoic acid corresponding to the monomer unit in the medium.

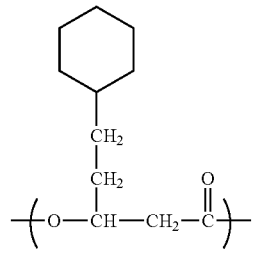

(18)

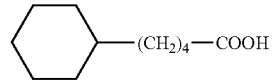

(19)

An initial content of the alkanoic acid added to the medium is preferably selected to be the range of 0.01% to 1% (w/v) per medium, more preferably in the range of 0.02% to 0.2% (w/v) per medium.

A culture process for allowing a microorganism to produce and accumulate a PHA may be one in which microbial cells are transferred to a medium with restriction on a nitrogen source such as ammonium chloride after the microorganism is sufficiently grown. An increase in productivity may be observed when the microorganism is further cultured in a state where a compound to be provided as a substrate of the desired unit is added to the medium. For example, a multistage system in which two or more steps under different culture conditions are connected to each other can be employed.

More concretely, one of the methods is carried out as follows. As a first culture step (Culture Step 1), a step of culturing a microorganism that contains an alkanoic acid as a raw material and saccharide as a growth substrate is continuously carried out from a late stage of a logarithmic growth phase to a stationary growth phase. Then, the microbial cells are temporally collected by centrifugation or the like, followed by performing a second culture step (Culture Step 2). In Culture Process 2, the microbial cells cultured and grown in Culture Process 1 are further cultured in a medium (preferably, the medium is free of nitrogen source).

A culture temperature may be within a range that allows favorable growth of the microbial strain. For example, the culture temperature is in the range of 15 to 40° C., preferably of 20 to 35° C., more preferably of 20 to 30° C.

Each of the above culture processes including liquid culture and solid culture may be used as far as the microorganism to be used grows to produce a PHA having a monomer unit represented by the general formula (1) from an alkanoic acid provided as a raw material in a medium with the method used. Furthermore, the culture may be of any type such as batch culture, fed batch culture, semi-continuous culture, or continuous culture as far as a raw material, a growth substrate, and oxygen can be properly supplied. For example, liquid batch culture may be designed such that oxygen can be supplied into a medium by shaking a shaking flask or by ventilating air with agitation in a jar fermentor.

Any inorganic medium can be used in the above culture processes as far as the inorganic medium contains a component necessary for the growth of a microorganism, such as a phosphorus source (e.g., phosphate) or a nitrogen source (e.g., ammonium salt or nitrate). Thus, examples of the inorganic culture medium include an MSB medium and an M9 medium.

For instance, the composition of the M9 medium used in the examples described later is described below.

M9 Medium
    $Na_2HPO_4$: 6.2 g
    $KH_2PO_4$: 3.0 g
    NaCl: 0.5 g
    $NH_4Cl$: 1.0 g
    (In 1 liter of the medium, pH 7.0)

Furthermore, for achieving a favorable growth of the microorganism and the PHA production associated therewith, a trace element solution described below may be added to the mineral medium at a concentration of about 0.3% (v/v) to make up for essential trace elements.

Trace Element Solution
    nitrilotriacetic acid: 1.5 g;
    $MgSO_4$: 3.0 g;
    $MnSO_4$: 0.5 g;
    NaCl: 1.0 g;
    $FeSO_4$: 0.1 g;
    $CaCl_2$: 0.1 g;
    $CoCl_2$: 0.1 g;
    $ZnSO_4$: 0.1 g;
    $CuSO_4$: 0.1 g;
    $AlK(SO_4)_2$: 0.1 g;
    $H_3BO_3$: 0.1 g;
    $Na_2MoO_4$: 0.1 g;
    $NiCl_2$: 0.1 g
    In 1 liter of the medium, pH 7.0

Process of Recovering PHA

The microorganism used in the present invention produces a PHA containing a monomer unit represented by the general formula (1) and accumulates the PHA in its microbial cells by the culture process described above. Thus, the production process for a PHA of the present invention further includes a step of isolating and recovering the desired PHA from the cultured microbial cells after culture.

The recovery of a PHA from the cultured microbial cells of the microorganism can be performed by applying means for isolating and recovering the solubilized PHA from insoluble components derived from the cells using a solvent extraction method. A chloroform extraction typically performed in the art is the simplest. In the extraction, as an alternative to chloroform, dichloromethane, dioxane, tetrahydrofuran, acetonitrile, acetone, or the like may be used. Under an environment where an organic solvent cannot be easily used, it is possible to apply a process of recovering only a PHA as an insoluble fraction by solubilizing and removing intracellular components except the PHA by means of a treatment with a surfactant such as SDS or a treatment with an enzyme such as lysozyme. Alternatively, it is possible to apply a process of isolating and recovering only a PHA accumulated in microbial cells by crushing the microbial cells with an ultrasonic crushing method, a homogenization method, a pressure crushing method, a bead impact method, a grinding method, a pulverizing method, a freeze-thawing method, or the like.

Furthermore, in the production process for the PHA of the present invention, the microbial culture is not limited to any of those described above. In addition, the steps of producing and accumulating the PHA in the microorganism being cultured in the culture, and recovering the PHA from the microbial cells after the culture of the microorganism are also not limited to those described above.

The PHA to be produced by the process of the present invention may contain a 3-hydroxyalkanoate unit biosynthesized through a fatty acid synthesis system utilizing a growth substrate to be added to the medium in addition to the monomer unit represented by the general formula (1). By the way, in any of the 3-hydroxyalkanoate units, the carbon atom at position 3 is an asymmetric carbon atom and the absolute configuration thereof is the R configuration. Thus, it is a matter of course that the PHA unit retains its biodegradability. Having the monomer unit represented by the general formula (1) provides the polymer with its new physicochemical property. Thus, there is a possibility of improving the physical properties of such a polymer, so that the development of the polymer to another field on which the polymer has not been applied can be expected.

Binder Resin

The binder resin to be used for an electrostatic charge image-developing toner of the present invention contains at least a PHA having a monomer unit represented by the general formula (1) in its polymer molecule. In addition, the binder resin may have another PHA that further contains at least one selected from the group consisting of monomer units represented respectively by the general formulae (2) and (3) in its polymer molecule in addition to the monomer unit represented by the general formula (1).

Furthermore, the binder resin may be a binder resin further containing one or more kinds of biodegradable resins such as polycaprolactone and a polylactic acid.

The polylactic acid may be one of those commercially available, such as Lacty (trade name) manufactured by Shimadzu Corporation, or one of those obtained by various polymerization methods.

When other biodegradable resin is used together, the biodegradable resin is mixed preferably at a percentage of 90% by mass or less with respect to the whole of the binder resin in consideration of the biodegradability and the physical properties of the binder resin.

A PHA having a number average molecular weight of about 300,000 or less is preferable because the PHA shows good compatibility with each of polycaprolactone and a polylactic acid and results in a transparent and colorless molten polymer blend. On the other hand, for a PHA having a comparatively large number average molecular weight of, for example 500,000 or more, its compatibility is not sufficiently increased and the color of the resulting molten polymer blend is no good. In this case, however, the compatibility of the PHA can be increased and a transparent and colorless molten polymer blend can be obtained by reducing the average molecular weight of the PHA to 300,000 or less by mixing under a high shearing force.

Furthermore, the number average molecular weight of the binder resin of the present invention is preferably 2,000 or more but 300,000 or less. Moreover, the glass transition temperature of the binder resin of the present invention is in the range of 30 to 80° C., and the softening point of the binder resin is preferably in the range of 60 to 170° C. for the functional expression of the binder resin.

Here, the PHA has a basic skeleton in the shape of a biodegradable resin. Therefore, like the conventional plastics, the PHA can be used for the production of various products by melt processing or the like, while having conspicuous characteristics different from synthetic macromolecules derived from petroleum. That is, the PHA can be easily biodegraded and incorporated into the material recycling in nature. Therefore, there is no need to subject the PHA to thermal disposal. The PHA is an effective material also from the viewpoint of preventing air pollution or global warming. In addition, the PHA can be used as plastics that make environmental preservation possible.

Furthermore, the PHA can be easily hydrolyzed in the presence of alkaline water. Therefore, the PHA has an advantage of efficiently removing a toner containing a pigment such as carbon black out of the copied paper.

The PHA containing the monomer unit represented by the general formula (1), which is suitable for a binder resin to be used for the electrostatic charge image-developing toner of the present invention, is a polyester resin having a 3-hydroxyalkanoic acid as a monomer unit and containing at least a cyclohexyl group as a substituent. Here, when such a compound is produced from the microorganism, the resulting polyester resin is an isotactic polymer composed only of the R configuration. If the object of the present invention can be achieved in both terms of physical properties and functions, the polyester resin is not necessary to be an isotactic polymer in particular. Alternatively, the polyester resin may be used for an atactic polymer. In addition, it is also possible to obtain the PHA by a chemical synthesis method in which a lactone compound is subjected to ring-opening polymerization with an organometallic catalyst (e.g., an organic catalyst containing aluminum, zinc, or tin).

In the present invention, with respect to the monomer unit represented by the general formula (1), what is important is that R1 can be one or more kinds of atoms selected from the group including a hydrogen atom and a fluorine atom. Here, with respect to the monomer unit represented by the general formula (1), its environmental dependency can be reduced more by making R1 as an aromatic ring substituted with a fluorine atom. In the case of substituting with the fluorine atom, the content of the monomer unit containing such a fluorine atom may be 1% by mole or more in the polymer, where the ratio of the fluorine atom to the polymer may be defined in consideration of the desired environmental dependency.

In addition, it is possible to obtain the polyhydroxyalkanoate constructed of the corresponding monomer unit even if the substitution position of R1 may be any of ortho, meta, and para positions. However, if there is no substantial difference between any of the isomers with respect to their functionality, physical properties, or the like, a substitute at a meta position or a para position may be suitably used because of its yield or the ease with which the substitute is incorporated into the polymer.

Here, when a PHA to be used for the binder resin of the present invention is produced using a microorganism, the PHA may contain various monomer units described above. The PHA may be designed to contain an appropriate number of monomer units in consideration of functionality, physical properties, and so on of the desired polymer.

The glass transition temperature of the PHA to be used for the binder resin of the present invention is preferably in the range of 30 to 80° C., more preferably of 40 to 80° C., still more preferably of 50 to 70° C. If the glass transition temperature is less than 30° C., the blocking tendency of the toner tends to be deteriorated. If the glass transition temperature is more than 80° C., the fixing ability of the toner tends to be deteriorated. Furthermore, the softening point of the PHA to be used for the binder resin of the present invention is preferably in the range of 60 to 170° C., particularly preferably of 80 to 140° C. If the softening point is less than 60° C., a deterioration in offset resistance of the toner can be observed. If the softening point is more than 170° C., the fixing temperature of the toner tends to be increased.

A PHA having those desired physical properties can be obtained by selecting the culture conditions or the like of the microorganism capable of synthesizing the PHA of the present invention. For instance, the number average molecular weight of the PHA can be controlled by controlling the culture period or the like. In addition, the number average molecular weight of the PHA can be controlled by removing a lower molecular weight component from the PHA by means of solvent extraction, reprecipitation, or the like. Here, the glass transition temperature and softening point correlate with the molecular weight of the PHA. In addition, the glass transition temperature and softening point can be controlled by controlling the type/composition ratio of the monomer unit in the PHA.

The PHA to be used for the binder resin of the present invention has a weight average molecular weight Mw of preferably 4,000 to 300,000 and a number average molecular weight Mn of preferably 2,000 to 300,000, particularly preferably 5,000 to 100,000. If the Mn is less than 2,000, the glass transition temperature can be extensively decreased and the resistance to blocking tendency deteriorates. If the Mn is more than 300,000, the viscosity of the toner is increased at the time of melting and the low temperature fixing ability of the toner deteriorates.

The binder resin of the present invention may preferably be used as a binder resin. However, in addition to the binder resin of the present invention, another thermoplastic resin may be included as a binder resin. For example, a mixture with one or two or more kinds of materials selected from the group consisting of: styrene polymers such as polystyrene, polyacrylate, and a styrene-acrylate copolymer; polyvinyl chloride; polyvinyl acetate; polyvinylidene chloride; a phenol resin; an epoxy resin; and a polyester resin may be used. In general, no particular limitation is imposed on the binder resins as long as the binder resins are ones to be used for toner production.

When a thermoplastic resin having no degradability is used as a binder resin in addition to the PHA, such an additional thermoplastic resin is mixed at a percentage of preferably 80% by mass or less, more preferably 50% by mass or less with respect to the whole of the binder resin. If the percentage of the additional thermoplastic resin is more than 80% by mass, the binding strength of the additional thermoplastic resin to the surface of paper becomes too strong, so that the deinking property of the binder resin can be decreased. Furthermore, if the binder resin is used for a biodegradable toner, it is not preferable to mix the PHA with other thermoplastic resin having no biodegradability.

Furthermore, in the present invention, the binder resin can be used by preferably mixing with each of various biodegradable plastics, which are commercially available, including "Ecoster" and "Ecostar Plus" (Hagiwara Industries, Inc.), "Biopol" (ICI Japan), "Ajicoat" (Ajinomoto Co., Ltd.), "Placcel" and "Polycaprolactone" (Daicel Chemical Industries, Ltd.), "Sholex" (Showa Denko K.K.) and "Bionolle" (Highpolymer Co.,Ltd.), "Lacty" (Shimadzu Corporation), and "Lacea" (Mitsui Chemicals, Inc.). In the case of using those resins as a mixture thereof, the biodegradability characteristic of the toner of the present invention hardly deteriorates.

Among them, the polycaprolactone (e.g., a polymer of ε-caprolactone) and the polylactic acid described above are particularly preferable in that the polycaprolactone and the polylactic acid can be easily and completely decomposed by the action of lipase, esterase, or the like, and their physical properties can be modified by blending, copolymerizing, or the like with other resin.

Examples of the styrene polymers include: a copolymer of styrene and (metha)acrylate and a copolymer of another monomer having a copolymerization ability to those; and a copolymer of styrene and a diene monomer (such as butadiene or isoprene) and a copolymer of another monomer having a copolymerization ability to those. Examples of the polyester polymers include a condensation polymer of an aromatic dicarboxylic acid and an aromatic diol alkylene oxide additive. Examples of the epoxy polymers include a reactant of an aromatic diol and epichlorohydrin, and modified products thereof. Examples of the polyolefin polymers include polyethylene, polypropylene, and a copolymer chain of those compounds with another copolymerizable monomer. Examples of the polyurethane polymers include a polyadditive of an aromatic diisocyanate and an aromatic diol alkylene oxide additive.

Specific examples of the binder resin to be used as a mixture with the binder resin of the present invention include: polymers of polymerizable monomers described below; mixtures thereof; and copolymerized products obtained by using two or more kinds of polymerizable monomers described below. Specifically, as such a binder resin, a styrene polymer such as a styrene-acrylate copolymer or a styrene-methacrylate copolymer, a polyester polymer, an epoxy polymer, a polyolefin polymer, or a polyurethane polymer can be preferably used.

Specific examples of the polymerizable monomers include: styrene and derivatives thereof such as styrene, o-methylstyrene, m-methylstyrene, p-methylstyrene, p-methoxystyrene, p-phenylstyrene, p-chlorostyrene, 3,4-dichlorostyrene, p-ethylstyrene, 2,4-dimethylstyrene, p-n-butylstyrene, p-tert-butylstyrene, p-n-hexylstyrene, p-n-octylstyrene, p-n-nonylstyrene, p-n-decylstyrene, and p-n-dodecylstyrene; ethylenically unsaturated monoolefins such as ethylene, propylene, butylene, and isobutylene; unsaturated polylenes such as butadiene; halogenated vinyls such as vinyl chloride, vinylidene chloride, vinyl bromide, and vinyl fluoride; vinyl esters such as vinyl acetate, vinyl propionate, and vinyl benzoate; .alpha.-methylene aliphatic monocarboxylates such as methyl methacrylate, ethyl methacrylate, propyl methacrylate, n-butyl methacrylate, isobutyl methacrylate, n-octyl methacrylate, dodecyl methacrylate, 2-ethylhexyl methacrylate, stearyl methacrylate, phenyl methacrylate, dimethylaminoethyl methacrylate, and diethylaminoethyl methacrylate; acrylates such as methyl acrylate, ethyl acrylate, n-butyl acrylate, isobutyl acrylate, propyl acrylate, n-octyl acrylate, dodecyl acrylate, 2-ethyihexyl acrylate, stearyl acrylate, 2-chloroethyl acrylate, and phenyl acrylate; vinyl ethers such as vinyl methyl ether, vinyl ethyl ether, and vinyl isobutyl ether; vinyl ketones such as vinyl methyl ketone, vinyl hexyl ketone, and methyl isopropenyl ketone; N-vinyl compounds such as N-vinylpyrrole, N-vinylcarbazole, N-vinylindole, and N-vinyl pyrrolidone; vinylnaphthalenes; acrylic acid derivatives or methacrylic acid derivatives such as acrylonitrile, methacrylonitrile, and acrylamide; esters of the above-described α, β-unsaturated acids and diesters of the above-described dibasic acids; dicarboxylic acids such as maleic acid, methyl maleate, butyl maleate, dimethyl maleate, phthalic acid, succinic acid, and terephthalic acid; polyol compounds such as ethylene glycol, diethylene glycol, triethylene glycol, 1,2-propylene glycol, 1,3-propylene glycol, 1,4-butanediol, 1,6-hexanediol, bisphenol A, hydrogenated bisphenol A, and polyoxyethylenated bisphenol A; isocyanates such as p-phenylene dilsocyanate, p-xylylene diisocyanate, and 1,4-tetramethylene diisocyanate; amines such as ethylamine, butylamine, ethylenediamine, 1,4-diaminobenzene, 1,4-diaminobutane, and monoethanolamine; and epoxy compounds such as diglycidyl ether, ethyleneglycol diglycidyl ether, bisphenol A glycidyl ether, and hydroquinone diglycidyl ether.

When forming a binder resin to be used by mixing the binder resin of the present invention, the following crosslinking agents may be used if required. Examples of the bifunctional crosslinking agents include divinylbenzene, bis(4-acryloxypolyethoxyphenyl)propane, ethylene glycol diacrylate, 1,3-butylene glycol diacrylate, 1,4-butanediol diacrylate, 1,5-pentanediol diacrylate, 1,6-hexanediol diacrylate, neopentyl glycol diacrylate, diethylene glycol diacrylate, triethylene glycol diacrylate, tetraethylene glycol diacrylate, polyethylene glycol diacrylate #200, polyethylene glycol diacrylate #400, polyethylene glycol diacrylate #600, dipropylene glycol diacrylate, polypropylene glycol diacrylate, polyester-type diacrylates (MANDA, manufactured by Nippon Kayaku Co., Ltd.), and compounds obtained by substituting the methacrylate of the above compounds for the acrylate.

Examples of the polyfunctional crosslinking agent having two or more functionalities include pentaerythritol acrylate, trimethylolethane triacrylate, trimethylolpropane triacrylate, tetramethylolmethane tetraacrylate, oligoester acrylate, and those obtained by substituting methacrylate of the above compounds for acrylate, 2-2-bis(4-methacryloxy polyethoxyphenyl)propane, diallyl phthalate, triallyl cyanurate, triallyl isocyanurate, triallyl isocyanurate, triallyl trimellitate, and diaryl chlorrendate.

Further, when forming a binder resin to be used by mixing the binder resin of the present invention, the following polymerization initiators may be used if required. Examples of the polymerization initiator include t-butylperoxy-2-ethylhexanoate, cumin perpivalate, t-butylperoxy laurate, benzoyl peroxide, lauroyl peroxide, octanoyl peroxide, di-t-butyl peroxide, t-butylcumyl peroxide, dicumyl peroxide, 2,2'-azobis isobutyronitrile, 2,2'-azobis-(2-methylbutyronitrile), 2,2'-azobis-(2,4-dimethylvaleronitrile), 2,2'-azobis(4-methoxy-2,4-dimethylvaleronitrile), 1,1-bis(t-butylperoxy) 3,3,5-trimethylcyclohexane, 1,1-bis(t-butylperoxy)cyclohexane, 1,4-bis(t-butylperoxycarbonyl)cyclohexane, 2,2-bis(t-butylperoxy)octane, n-butyl 4,4-bis(t-butylperoxy)valerate, 2,2-bis(t-butylperoxy)butane, 1,3-bis(t-butylperoxy-isopropyl)benzene, 2,5-dimethyl-2,5-di(t-butylperoxy)hexane, 2,5-dimethyl-2,5-di(t-butylperoxy)hexane, 2,5-dimethyl-2,5-di(benzoylperoxy)hexane, di-t-butyldiperoxy isophthalate, 2,2-bis-(4,4-di-t-butylperoxycyclohexyl)propane, di-t-butylperoxy a-methylsuccinate, di-t-butylperoxy dimethylglutarate, di-t-butylperoxy hexahydroterephthalate, di-t-butylperoxy azelate, 2,5-dimethyl-2,5-di(t-butylperoxy) hexane, diethylene glycol-bis(t-butylperoxycarbonate), di-t-butylperoxy trimethyladipate, tris(t-butylperoxy)triazine, and vinyltris(t-butylperoxy)silane. Those may be used either singly or in any combination thereof. The amount of the polymerization initiator to be used is 0.05 parts by mass or more (preferably 0.1 to 15 parts by mass) with respect to 100 parts by mass of a monomer.

Toner

The electrostatic charge image-developing toner of the present invention is constructed of a colorant, a charge control agent, and other additives to be added if required in addition to the binder resin described above.

Colorant

The colorant provided as one of the components in the electrostatic charge image-developing toner of the present invention is not particularly limited as far as the colorant is generally used for the production of a toner in the art. Examples of the colorant include carbon black, titanium white, a monoazo red, a disazo yellow pigment, a quinacridone magenta pigment, and an anthraquinone dye. In other words, various kinds of pigments and/or dyes can be used.

More specifically, examples of the colorant when using the electrostatic charge image-developing toner of the present invention as a magnetic color toner include C.I. Direct Red 1, C.I. Direct Red 4, C.I. Acid Red 1, C.I. Basic Red 1, C.I. Mordant Red 30, C.I. Direct Blue 1, C.I. Direct Blue 2, C.I. Acid Blue 9, C.I. Acid Blue 15, C.I. Basic Blue 3, C.I. Basic Blue 5, C.I. Mordant Blue 7, C.I. Direct Green 6, C.I. Basic Green 4, and C.I. Basic Green 6. Examples of the pigments include Chrome Yellow, Cadmium Yellow, Mineral Fast Yellow, Navel Yellow, Naphthol Yellow S, Hansa Yellow G, Permanent Yellow NCG, Tartrazine Lake, Chrome Orange, Molybdenum Orange, Permanent Orange GTR, Pyrazolone Orange, Benzidine Orange G, Cadmium Red, Permanent Red 4R, Watching Red Calcium Salt, Eosine Lake, Brilliant Carmine 3B, Manganese Purple, Fast Violet B, Methyl Violet Lake, Prussian Blue, Cobalt Blue, Alkali Blue Lake, Victoria Blue Lake, Phthalocyanine Blue, Fast Sky Blue, Indanthrene Blue BC, Chrome Green, Chrome Oxide, Pigment Green B, Malachite Green Lake, and Final Yellow Green G.

Further, the following colorants may be used when using the electrostatic charge image-developing toner of the present invention as a two-component full color toner. Examples of the color pigments for magenta toner include: C.I. Pigment Red 1, 2, 3, 4, 5, 6, 7, 8, 9, 10, 11, 12, 13, 14, 15, 16, 17, 18, 19, 21, 22, 23, 30, 31, 32, 37, 38, 39, 40, 41, 48, 49, 50, 51, 52, 53, 54, 55, 57, 58, 60, 63, 64, 68, 81, 83, 87, 88, 89, 90, 112, 114, 122, 123, 163, 202, 206, 207, and 209; C.I. Pigment Violet Red 19; and C.I. Vat Red 1, 2, 10, 13, 15, 23, 29, and 35.

Although the above-described pigments may be used singly in the present invention, it is more preferable to combine a dye and a pigment to improve definition of an image from the viewpoint of image quality of a full color image. Examples of the dyes for magenta available in that case include: oil-soluble dyes such as C.I. Solvent Red 1, 3, 8, 23, 24, 25, 27, 30, 49, 81, 82, 83, 84, 100, 109, and 121, C.I. Disperse Red 9, C.I. Solvent Violet 8, 13, 14, 21, and 27, and C.I. Disperse Violet 1; and basic dyes such as C.I. Basic Red 1, 2, 9, 12, 13, 14, 15, 17, 18, 22, 23, 24, 27, 29, 32, 34, 35, 36, 37, 38, 39, and 40, and C.I. Basic Violet 1, 3, 7, 10, 14, 15, 21, 25, 26, 27, and 28.

Other color pigments include color pigments for cyan. Examples thereof include: C.I Pigment Blue 2, 3, 15, 16, and 17; C.I. Vat Blue 6; C.I. Acid Blue 45; and a copper phthalocyanine pigment where any group of a phthalocyanine skeleton is substituted with 1 to 5 phthalimidemethyl groups.

Examples of the color pigments for yellow include: C.I Pigment Yellow 1, 2, 3, 4, 5, 6, 7, 10, 11, 12, 13, 14, 15, 16, 17, 23, 65, 73, and 83; and C.I Vat yellow 1, 3, and 20.

Each of the dyes and pigments described above may be used alone, or may be arbitrarily used in combination with others in order to acquire a desired color tone of the toner.

In addition, when the environmental preservation, the safety to the human body, and so on are taken into consideration, various kinds of food colors such as edible lakes can be suitably used. Examples of the edible lakes include Food Red No. 40 Aluminum Lake, Food Red No. 2 Aluminum Lake, Food Red No. 3 Aluminum Lake, Food Red No. 106 Aluminum Lake, Food. Yellow No. 5 Aluminum Lake, Food Yellow No. 4 Aluminum Lake, Food blue No. 1 Aluminum Lake, and Food blue No. 2 Aluminum Lake.

The water-insoluble food colors described above can also function as charge control agents. In that case, the aluminum lake can be suitably used for negative electrification. In the case where the water-insoluble food color has the function of a charge control agent, the food color can contribute to an improvement in environmental safety of the toner and to a cost reduction of the toner.

The content of the colorant in the toner may be changed extensively depending on the desired coloring effect or the like. Typically, for obtaining the most favorable characteristics of the toner, in other words, when the staining power of printing, the shape stability of the toner, the scattering of the toner, and so on are considered, each of the colorants is used at a concentration of about 0.1 to 60 parts by mass, preferably about 0.5 to 20 parts by mass with respect to 100 parts by mass of the binder resin.

Charge Control Agent

The charge control agents may be those conventionally used in the art. Specific examples of the charge control agents include a nigrosine dye, a quaternary ammonium salt, and a monoazo metal complex salt dye. The addition amount of the charge control agent can be defined in consideration of the conditions such as the electrostatic property of the binder resin, the production process including the addition amount and dispersion process of the colorant, and the electrostatic properties of other additives. However, the charge control agent can be used at a concentration of 0.1 to 20 parts by mass, preferably 0.5 to 10 parts by mass with respect to 100 parts by mass of the binder resin. In addition, inorganic particles such as those of a metal oxide or an inorganic material surface-treated with the organic material may be used. Those charge control agents may be used being by being added and mixed in the binder resin or being attached on the surface of toner particles.

Other Components

In addition to the binder resin and the colorant, the electrostatic charge image-developing toner of the present invention may further contain any one of the following compounds. Examples of the compounds include a silicone resin, polyester, polyurethane, polyamide, an epoxy resin, polyvinyl butyral, rosin, denatured rosin, a terpene resin, a phenol resin, an aliphatic or cycloaliphatic hydrocarbon resin such as a low-molecular weight polyethylene or a low-molecular weight polypropylene, an aromatic petroleum resin, chlorinated paraffin, and a paraffin wax. Among them, in particular, the waxes preferably used are the low-molecular weight polypropylene and a by-product thereof, the low-molecular weight polyester and ester wax, and the aliphatic derivative. Of those waxes, those classified with their molecular weights by various methods may be also preferably used in the present invention. In addition, after the classification, the acid value of the classified wax may be changed or the wax may be subjected to block copolymerization or graft denaturation.

In particular, the electrostatic charge image-developing toner of the present invention becomes a toner having excellent characteristics when the wax components are included in the toner, and are dispersed substantially like a globular shape and/or spindle-island shape in the binder resin under tomographic observation on the toner using a transmission electron microscope.

Toner Production Process

A specific process for preparing the electrostatic charge image-developing toner of the present invention having the structure as described above may be any of the conventional processes known in the art. The electrostatic charge image-developing toner of the present invention can be prepared, for example using the so-called pulverization process for obtaining a toner by the following steps. Specifically, resins such as the binder resin of the present invention and other components to be added if required such as a charge control agent and wax are sufficiently mixed in a mixer such as Henschel mixer or a ball mill, followed by melt-kneading the mixture using a heat-kneading machine such as a heating roller, a kneader, or an extruder to compatibilize the resins with each other. Then, additives such as a pigment, a dye or a magnetic substance as a colorant, and a metallic compound to be added if required are dispersed or dissolved in the mixture. After the mixture is cooled for solidification, the solidified product is pulverized with a pulverizer such as a jet mill or a ball mill, and is then classified to obtain an electrostatic charge image-developing toner of the present invention having a desired particle size. In the above-mentioned classification step, for production efficiency, a multidivision classifier is preferably used.

Alternatively, the binder resin, the charge control agent, and so on are mixed in solution using a solvent (e.g., an aromatic hydrocarbon such as toluene or xylene, a halide such as chloroform or ethylene dichloride, a ketone such as acetone or methyl ethyl ketone, or an amide such as dimethylformamide). After an agitating treatment, the mixture is poured and precipitated in water, followed by being filtrated and dried to solidify the mixture. Then, the solidified product is pulverized with a pulverizer such as a jet mill or a ball mill, and is then classified to obtain an electrostatic charge image-developing toner of the present invention having a desired particle size. In the above-mentioned classification step, for production efficiency, a multidivision classifier is preferably used.

Furthermore, the electrostatic charge image-developing toner of the present invention can be also prepared by the so-called polymerization method as described below. That is, in this case, materials including: a polymerizable monomer of the binder resin of the present invention; a pigment, a dye, or a magnetic substance as a colorant; and other additives such as a cross-linking agent, a polymerization initiator, and a wax if required are mixed and dispersed. Then, the mixture is suspended and polymerized in an aqueous dispersion medium in the presence of a surfactant or the like to synthesize polymerizable colored resin particles. The resulting particles are subjected to solid-liquid separation, followed by being dried and then classified if required to obtain an electrostatic charge image-developing toner of the present invention.

Silica External Additive

In the present invention, it is preferable to externally add silica fine powders to the toner prepared by the process described above for increasing electrostatic stability, developing property, flow property, and durability. The silica fine powders to be used herein will impart good results when the specific surface area of the powders is 20 $m^2/g$ or more (particularly of 30 to 400 $m^2/g$) obtained by nitrogen adsorption measured by the BET method. In this case, the amount of the silica fine powders to be used is in the range of 0.01 to 8 parts by mass, preferably of about 0.1 to 5 parts by mass with respect to 100 parts by mass of the toner particles. The silica fine powders used in this case is preferably those treated with a treating agent for hydrophobing the toner and controlling the electrostatic property of the toner. Examples of the treating agent include a silicone varnish, various modified silicone varnishes, a silicone oil, various modified silicon oils, a silane coupling agent, a silane coupling agent having a functional group, and other organic silicon compounds. Those treating agents may be used in combination with each other.

Inorganic Powder

In order to improve the developing ability and durability of toner, the following inorganic powder may preferably be added. Preferred examples of the inorganic powder include: oxides of metals such as magnesium, zinc, aluminum, cerium, cobalt, iron, zirconium, chromium, manganese, strontium, tin, and antimony; composite metal oxides such as calcium titanate, magnesium titanate, and strontium titanate; metallic salts such as calcium carbonate, magnesium carbonate, and aluminum carbonate; clay minerals such as kaolin; phosphate compounds such as apatite; silicon compounds such as silicon carbide and silicon nitride; and carbon powder such as carbon black and graphite. Of those, fine powder of zinc oxide, aluminum oxide, cobalt oxide, manganese dioxide, strontium titanate, or magnesium titanate is preferably used.

Lubricant

In addition, the following lubricant powder may be added to toner. Examples of the lubricant powder include: fluorine resins such as Teflon (R) and polyvinylidene fluoride; fluorine compounds such as carbon fluoride; fatty acid metallic salts such as zinc stearate; a fatty acid and fatty acid derivatives such as fatty ester; and molybdenum sulfide.

The content of each of the binder resin, the colorant, the charge control agent, and other additives to be added if required, which are mixed with the binder resin of the present invention, in the toner is very small. In consideration of the process after disposal, however, it is more preferable to use those having biodegradability if possible.

With Regard to Carrier

The electrostatic charge image-developing toner of the present invention having the structure as described above can be applied to various kinds of toners conventionally known in the art, such as: a non-magnetic toner independently used as a non-magnetic mono-component developer or used for constructing a magnetic two-component developer together with a magnetic carrier; and a magnetic toner to be independently used as a magnetic mono-component toner. The carrier used in the two-component developing process is any of those conventionally known in the art. Specifically, particles having an average particle size of 20 to 300 µm, which are formed from any of surface-oxidized or nonoxidized metals such as iron, nickel, cobalt, manganese, chromium, and rare earth elements, and alloys or oxides thereof, can be used as carrier particles. In addition, the carrier used in the present invention is preferably one prepared such that the surface of the carrier particles is attached or coated with a material such as a styrene resin, an acrylic resin, a silicone resin, a fluorine resin, or a polyester resin.

Magnetic Toner

The electrostatic charge image-developing toner of the present invention may be a magnetic toner produced by adding a magnetic material to a toner particle. In this case, the magnetic material can also serve as a colorant. Examples of the magnetic material to be used in this case include: iron oxides such as magnetite, hematite, and ferrite; metals such as iron, cobalt, and nickel; alloys of those metals and metals such as aluminum, cobalt, copper, lead, magnesium, tin, zinc, antimony, beryllium, bismuth, cadmium, calcium, manganese, selenium, titanium, tungsten, and vanadium; and mixtures thereof. The average particle size of the magnetic material that can be used in the present invention is 2 µm or less, preferably about 0.1 to 0.5 µm. The amount of the magnetic material to be added to toner is preferably 20 to 200 parts by mass with respect to 100 parts by mass of a binder resin, particularly preferably 40 to 150 parts by mass with respect to 100 parts by mass of a binder resin.

In order to achieve a higher image quality, there is a need of making possible to faithfully develop a smaller latent image dot. Thus, for example, it is preferable to adjust the weight average particle size of the toner particles of the present invention for electrostatic charge image development to be within the range of 4 to 9 µm. In other words, it is not preferable when the weight average particle size of the toner particles is less than 4 µm because a decrease in transferring efficiency occurs. In this case, furthermore, transfer residual toner tends to remain in large quantity on the photosensitive body and also tends to be responsible for an uneven image based on fogging and transferring fault. In addition, when the weight average particle size of the toner particles is more than 9 µm, the dropouts of character and line images tend to occur.

In the present invention, the average particle size and particle size distribution of the toner were measured using Coulter counter TA-II or Coulter multisizer (manufactured by Beckman Coulter, Inc.) connected to an interface (manufactured by Nikkaki Bios Co., Ltd.) and a personal computer for outputting number distribution and volume distribution. As an electrolytic solution to be used in that case, a 1% NaCl aqueous solution is prepared using a primary sodium chloride. For instance, the electrolytic solution may be a commercially-available ISOTONR-II (manufactured by Coulter Scientific Japan, Co., Ltd.). In a specific measuring method, a test sample is prepared as follows. 0.1 to 0.5 ml of a surfactant (preferably alkylbenzene sulfonate) is added as a dispersing agent into 100 to 150 ml of the electrolytic solution, and then 2 to 20 mg of a test portion is added in the mixture to provide a test sample. The measurement was carried out such that the electrolytic solution in which the test sample was suspended was subjected to a dispersion treatment with an ultrasonic disperser for about 1 to 3 minutes. Then, using a 100-µm aperture as an aperture, the volume and number of toner particles each having a particle size of 2 µm or more were calculated using the Coulter counter TA-II to compute the volume distribution and number distribution of the toner. Subsequently, a weight average particle size (D4) of the toner on the basis of a volume standard was determined from the volume distribution of the present invention, and a length average particle size (D1) on the basis of a number standard was determined from the number distribution of the present invention.

Charging Quantity

In the electrostatic charge image-developing toner of the present invention, for improving the transferring efficiency of the toner in a transferring process using a transferring member to which a voltage is applied, it is preferable that the charging quantity per unit mass (two-component process) be in the range of −10 to −80 µC/g, more preferably −15 to −70 µC/g.

Figure 9:
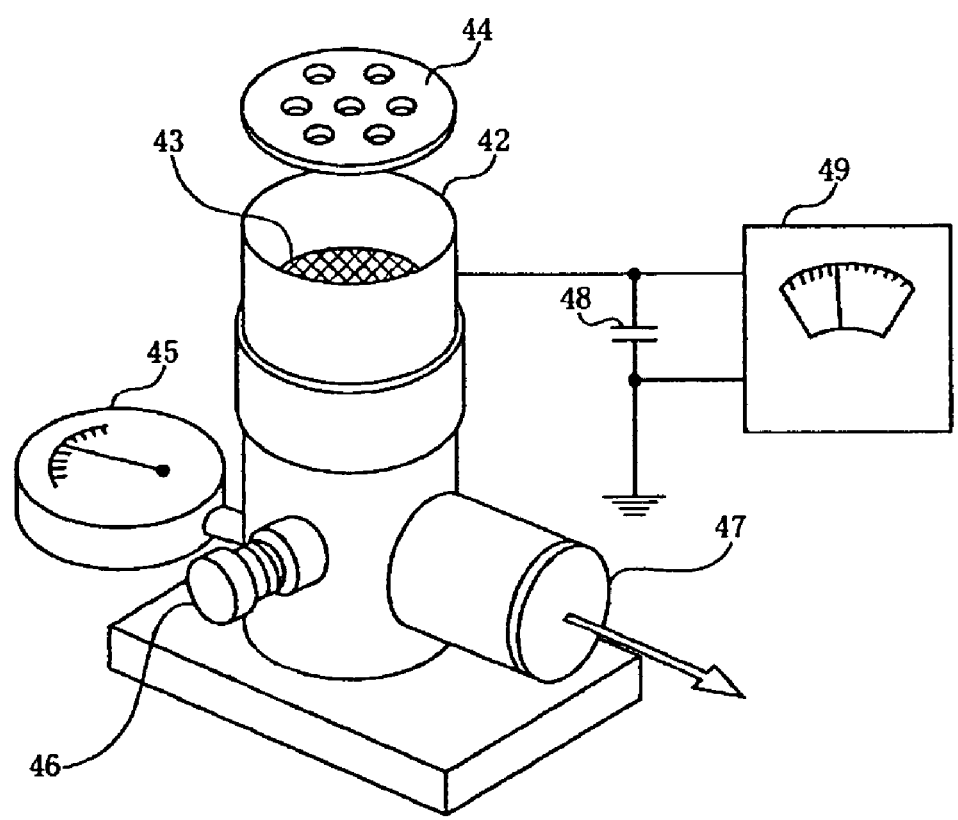
FIG. 9 is a schematic diagram showing a blow-off charging quantity measuring device for measuring a charging quantity of a toner.

The method of measuring the charging quantity by the two-component process used in the present invention (two-component triboelectricity) is described as follows. A charging quantity measuring device, shown in FIG. 9, is used for the measurement. At first, in a constant environment, EFV200/300 (manufactured by Powder-tech Co., Ltd.) is used as a carrier, and then a mixture prepared by adding 0.5 g of a measurement-target toner to 9.5 g of the carrier is placed in a polyethylene bottle of 50 to 100 ml in volume. Subsequently, the polyethylene bottle is mounted on a shaker with a constant amplitude under the shaking conditions of 100 mm in amplitude and 100 strokes per minute in shaking speed, followed by shaking for a predetermined time period. Then, 1.0 to 1.2 g of the mixture is placed in a measuring container 42 made of a metal with a 500-mesh screen 43 on the bottom of the charging quantity measuring device shown in FIG. 9, followed by being closed with a metallic lid 44. The mass of the whole measuring container 42 at that time was defined as a weighing capacity W1 (g). Then, the mixture is absorbed from a suction opening 47 with an aspirator (not shown, at least a portion to be in contact with the measuring container 42 is an insulating body). Then, an air-flow control valve 46 is adjusted such that a vacuum meter 45 indicates a pressure of 2450 Pa (250 mmAq). Under such conditions, the toner is sucked for one minute and then removed by absorption. A potential (volt) of an electrometer 49 at that time is denoted by V. Here, reference numeral 48 denotes a capacitor and a capacity thereof is defined as C (µF). Then, after sucking, the mass of the whole measuring device is measured and defined as W2

(g). A frictional charging quantity (μC/g) of the toner is calculated using the following equation from those measurements.

Calculating Equation: Frictional charging quantity $(\mu C/g) = C \times V/(W1-W2)$.

Method of Measuring Molecular Weight of Binder Resin

In the present invention, the molecular weight of the binder resin was measured using gel permeation chromatography (GPC). As a specific measuring method using the GPC, a sample was obtained by extracting a toner in a tetrahydrofuran (THF) solvent for 20 hours using Soxhlet extractor in advance, and was then used for the measurement. A column was constructed by connecting A-801, 802, 803, 804, 805, 806, and 807 manufactured by Showa Denko K.K. and an analytical curve of a standard polystyrene resin was used to measure the molecular weight distribution. In the present invention, furthermore, it is preferable to use a binder resin with a ratio (Mw/Mn) of a weight average molecular weight (Mw) to a number average molecular weight (Mn) measured as described above in the range of 2 to 100.

Glass transition temperature of toner

It is preferable that the toner of the present invention be prepared using suitable materials such that the glass transition temperature (Tg) of the toner is in the range of 30 to 80° C., more preferably of 50 to 70° C. in terms of fixing ability and storage stability. In this case, for example, the measurement of the glass transition temperature (Tg) may be performed using a high-precise differential scanning calorimeter of an internal combustion input compensation type, such as DSC-7 (manufactured by Perkin-Elmer Inc.). The measuring method is based on ASTMD 3418-82. In the present invention, for measuring the glass transition temperature (Tg), the following procedure is performed. The test sample is heated once to obtain the whole history thereof. Then, the test sample is rapidly cooled and is then heated again under the conditions including a heating rate of 10° C./min and a temperature ranging from 0 to 200° C. Thus, a DSC curve is measured at this time. It is recommended that the DSC curve be used for measuring Tg.

Image-forming Method and Apparatus

Particularly preferable is to apply the electrostatic charge image-developing toner having the configuration described above to an image-forming method including the steps of: charging an electrostatic latent image bearing member by externally applying a voltage to a charging member; forming an electrostatic charge image on the charged electrostatic latent image bearing member; developing the electrostatic charge image with a toner to form a toner image on the electrostatic latent image bearing member; transferring the toner image on the electrostatic latent image bearing member to a recording medium; and thermally fixing the toner image on the recording medium. Alternatively, in the image-forming method, the transferring step includes: a first transferring step of transferring the toner image on the electrostatic latent image bearing member to an intermediate transferring body; and a second transferring step of transferring the toner on the intermediate transferring body to the recording medium.

The image-forming apparatus used in such a method preferably includes the means corresponding to the respective steps, i.e., means for charging, means for forming an electrostatic charge image, means for developing, means for transferring, and means for thermally fixing.

Hereinafter, the present invention is described more specifically by way of examples. Each of these examples is one of the best embodiments of the present invention. However, the present invention is not limited to these examples. Here, "%" in the following description means % by weight, unless otherwise stated. In addition, the number of parts in the following composition corresponds to "parts by mass".

EXAMPLE 1

*Pseudomonas cichorii* strain YN2 was inoculated in an M9 medium (200 ml) containing 0.5% of D-glucose and 6.0 mM of 3-cyclohexylpropionic acid, and the whole was then subjected to shaking culture with 125 strokes/min. at 30° C. After 41 hours, the microbial cells were recovered by centrifugation. Subsequently, the recovered cells were resuspended in an M9 medium (200 ml) containing 0.5% of D-glucose and 6.0 mM of 3-cyclohexylpropionic acid in the absence of a nitrogen source (NH$_4$Cl). Then, the medium was subjected to shaking culture with 125 strokes/min. at 30° C. After 48 hours, the microbial cells were recovered by centrifugation, followed by washing with cold methanol once and drying in vacuo.

Furthermore, the dried microbial cell pellet was suspended in 20 ml of chloroform. Then, a PHA was extracted by agitating the suspension for 92 hours at 35° C. After the extract had been filtered with a membrane filter having a pore size of 0.45 μm, the filtrate was condensed with a rotary evaporator. Then, the concentrated solution was placed in cold methanol to precipitate the PHA therein again, followed by recovering a precipitate only and drying in vacuo.

The resultant PHA was evaluated for average molecular weight by gel permeation chromatography (GPC; Tosoh HLC-8220, column; Tosoh TSK-GEL Super HM-H, solvent; chloroform, in polystyrene equivalent). As a result, the number average molecular weight Mn was 46,000, and the mass average molecular weight w was 98,000.

For specifying the structure of the resultant PHA, an NMR analysis was carried out under the following conditions.

Measuring Apparatus

FT-NMR: Bruker DPX400

Resonance frequency: $^1H$=400 MHz, $^{13}C$=100 MHz

Measuring Condition

Measuring nuclide: $^1H$

Used solvent: CDCl$_3$

Measuring temperature: room temperature

A $^1H$-NMR spectrum chart obtained by the measurement is shown in FIG. 1.

Figure 2:
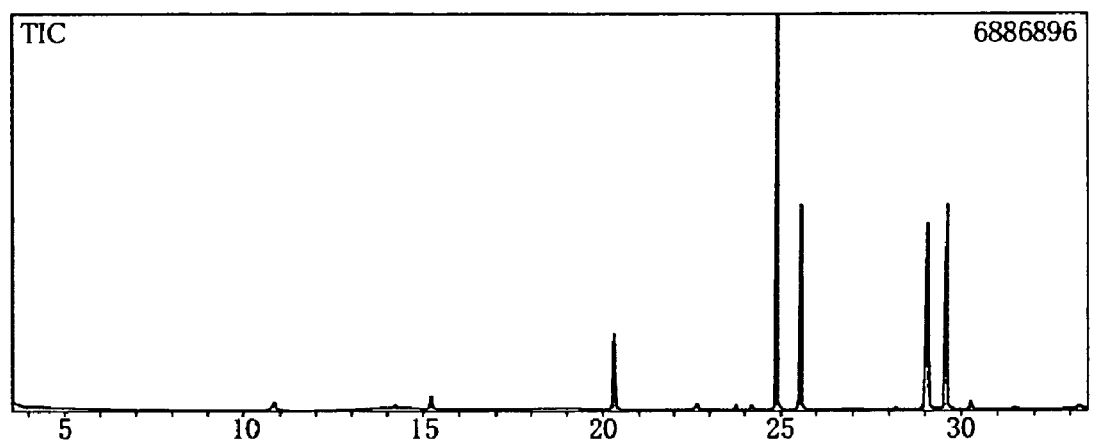
FIG. 2 is a total ion chromatogram (TIC) obtained by GC-MS measurement of a methylesterified product of a monomer unit structuring the PHA obtained in Example 1.
Figure 3:
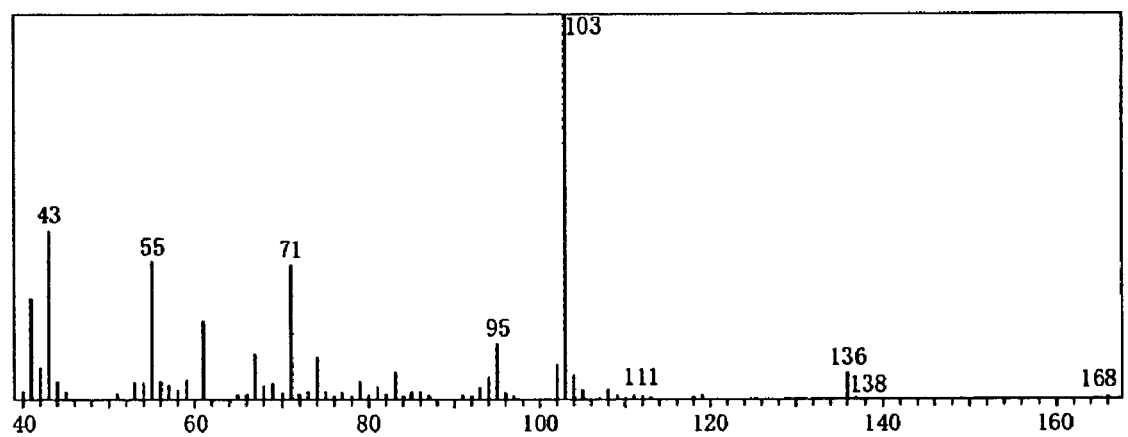
FIG. 3 is a mass spectrum of 3-hydroxy-3-cyclohexyl-propionate methylester obtained by the GC-MS measurement of the methylesterified product of the monomer unit structuring the PHA obtained in Example 1.

Furthermore, the obtained PHA was subjected to a methanolysis according to the conventional method, followed by being analyzed with a gas chromatography-mass spectrometer (GC-MS, Shimadzu QP-5050, EI method) to identify a methylesterified product of the monomer unit of the PHA. FIG. 2 shows a total ion chromatogram (TIC), and FIG. 3 shows a mass spectrum with a peak (about 25.5) containing a 3-hydroxy-3-cyclohexylpropionate methylester derived from the desired unit. Table 1 shows the TIC ratio of each unit of the PHA computed from the dry weight of the microbial cells, the weight of the polymer, and the area ratio of the TIC.

TABLE 1

| | |
|---|---|
| Dry weight of the microbial cells (mg/L) | 690 |
| Weight of the polymer (mg/L) | 210 |
| Monomer unit composition (TIC peak area ratio) | |
| 3-hydroxybutyric acid | 0.3% |
| 3-hydroxyhexanoic acid | 1.1% |
| 3-hydroxyoctanoic acid | 6.7% |
| 3-hydroxynonanoic acid | 0.3% |
| 3-hydroxydecanoic acid | 35.6% |
| 3-hydroxydodecanoic acid | 17.0% |
| 3-hydroxydodecenoic acid | 19.9% |
| 3-hydroxy-3-cyclohexylpropionate | 19.1% |

The above results confirmed that the PHA contains a 3-hydroxy-3-cyclohexylpropionate unit.

EXAMPLE 2

*Pseudomonas cichorii* strain H45 was inoculated in an M9 medium (200 ml) containing 0.5% of D-glucose and 6.0 mM of 3-cyclohexylpropionic acid, and the whole was then subjected to shaking culture with 125 strokes/min. at 30° C. After 47 hours, the microbial cells were recovered by centrifugation. Subsequently, the recovered cells were resuspended in an M9 medium (200 ml) containing 0.5% of D-glucose and 6.0 mM of 3-cyclohexylpropionic acid in the absence of a nitrogen source (NH$_4$Cl). Then, the medium was subjected to shaking culture with 125 strokes/min. at 30° C. After 41 hours, the microbial cells were recovered by centrifugation, followed by washing with cold methanol once and drying in vacuo.

Furthermore, the dried microbial cell pellet was suspended in 20 ml of chloroform. Then, a PHA was extracted by agitating the suspension for 54 hours at 35° C. After the extract had been filtered with a membrane filter having a pore size of 0.45 μm, the filtrate was condensed with a rotary evaporator. Then, the concentrated solution was placed in cold methanol to precipitate the PHA therein again, followed by recovering a precipitate only and drying in vacuo.

The obtained PHA was subjected to a methanolysis according to the conventional method, followed by being analyzed with a gas chromatography-mass spectrometer (GC-MS, Shimadzu QP-5050, EI method) to identify a methylesterified product of the monomer unit of the PHA. As a result, as shown in Table 2, it was confirmed that the PHA contains a 3-hydroxy-3-cyclohexylpropionate unit.

TABLE 2

| | |
|---|---|
| Dry weight of the microbial cells (mg/L) | 530 |
| Weight of the polymer (mg/L) | 120 |
| Monomer unit composition (TIC peak area ratio) | |
| 3-hydroxyhexanoic acid | 0.5% |
| 3-hydroxyoctanoic acid | 12.4% |
| 3-hydroxynonanoic acid | 0.2% |
| 3-hydroxydecanoic acid | 48.9% |
| 3-hydroxydodecanoic acid | 8.6% |
| 3-hydroxydodecenoic acid | 8.9% |
| 3-hydroxy-3-cyclohexylpropionate | 20.5% |

EXAMPLE 3

*Pseudomonas jessenii* strain P161 was inoculated in an M9 medium (200 ml) containing 0.5% of D-glucose and 6.0 mM of 3-cyclohexylpropionic acid, and the whole was then subjected to shaking culture with 125 strokes/min. at 30° C. After 47 hours, the microbial cells were recovered by centrifugation. Subsequently, the recovered cells were resuspended in an M9 medium (200 ml) containing 0.5% of D-glucose and 6.0 mM of 3-cyclohexylpropionic acid in the absence of a nitrogen source (NH$_4$Cl). Then, the medium was subjected to shaking culture with 125 strokes/min. at 30° C. After 41 hours, the microbial cells were recovered by centrifugation, followed by washing with cold methanol once and drying in vacuo.

Furthermore, the dried microbial cell pellet was suspended in 20 ml of chloroform. Then, a PHA was extracted by agitating the suspension for 54 hours at 35° C. After the extract had been filtered with a membrane filter having a pore size of 0.45 μm, the filtrate was condensed with a rotary evaporator. Then, the concentrated solution was placed in cold methanol to precipitate the PHA therein again, followed by recovering a precipitate only and drying in vacuo.

The obtained PHA was subjected to a methanolysis according to the conventional method, followed by being analyzed with a gas chromatography-mass spectrometer (GC-MS, Shimadzu QP-5050, EI method) to identify a methylesterified product of the monomer unit of the PHA. As a result, as shown in Table 3, it was confirmed that the PHA contains a 3-hydroxy-3-cyclohexylpropionate unit.

TABLE 3

| | |
|---|---|
| Dry weight of the microbial cells (mg/L) | 530 |
| Weight of the polymer (mg/L) | 150 |
| Monomer unit composition (TIC peak area ratio) | |
| 3-hydroxyhexanoic acid | 0.9% |
| 3-hydroxyoctanoic acid | 13.1% |
| 3-hydroxydecanoic acid | 48.8% |
| 3-hydroxydodecanoic acid | 9.7% |
| 3-hydroxydodecenoic acid | 14.1% |
| 3-hydroxy-3-cyclohexylpropionate | 13.4% |

EXAMPLE 4

*Pseudomonas cichorii* strain YN2 was inoculated in an M9 medium (200 ml) containing 0.5% of polypeptone (manufactured by Nihon Pharmaceutical Co., Ltd.) and 6.0 mM of 3-cyclohexylpropionic acid, and the whole was then subjected to shaking culture with 125 strokes/min. at 30° C. After 65 hours, the microbial cells were recovered by centrifugation, followed by washing with cold methanol once and drying in vacuo.

Furthermore, the dried microbial cell pellet was suspended in 20 ml of chloroform. Then, a PHA was extracted by agitating the suspension for 44 hours at 35° C. After the extract had been filtered with a membrane filter having a pore size of 0.45 μm, the filtrate was condensed with a rotary evaporator. Then, the concentrated solution was placed in cold methanol to precipitate the PHA therein again, followed by recovering a precipitate only and drying in vacuo.

The obtained PHA was subjected to a methanolysis according to the conventional method, followed by being analyzed with a gas chromatography-mass spectrometer (GC-MS, Shimadzu QP-5050, EI method) to identify a methylesterified product of the monomer unit of the PHA. As a result, as shown in Table 4, it was confirmed that the PHA contains a 3-hydroxy-3-cyclohexylpropionate unit.

TABLE 4

| | |
|---|---|
| Dry weight of the microbial cells (mg/L) | 340 |
| Weight of the polymer (mg/L) | 13 |
| Monomer unit composition (TIC peak area ratio) | |
| 3-hydroxybutyric acid | 40.2% |
| 3-hydroxyhexanoic acid | 1.0% |
| 3-hydroxyoctanoic acid | 5.4% |
| 3-hydroxynonanoic acid | 1.5% |
| 3-hydroxydecanoic acid | 15.8% |
| 3-hydroxydodecanoic acid | 8.1% |
| 3-hydroxy-3-cyclohexylpropionate | 28.1% |

EXAMPLE 5

*Pseudomonas cichorii* strain YN2 was inoculated in an M9 medium (200 ml) containing 0.5% of yeast extract (manufactured by Oriental Yeast, Co., Ltd.) and 6.0 mM of 3-cyclohexylpropionic acid, and the whole was then subjected to shaking culture with 125 strokes/min. at 30° C. After 42 hours, the microbial cells were recovered by centrifugation, followed by washing with cold methanol once and drying in vacuo.

Furthermore, the dried microbial cell pellet was suspended in 20 ml of chloroform. Then, a PHA was extracted by agitating the suspension for 185 hours at 35° C. After the extract had been filtered with a membrane filter having a pore size of 0.45 μm, the filtrate was condensed with a rotary evaporator. Then, the concentrated solution was placed in cold methanol to precipitate the PHA therein again, followed by recovering a precipitate only and drying in vacuo.

The obtained PHA was subjected to a methanolysis according to the conventional method, followed by being analyzed with a gas chromatography-mass spectrometer (GC-MS, Shimadzu QP-5050, EI method) to identify a methylesterified product of the monomer unit of the PHA. As a result, as shown in Table 5, it was confirmed that the PHA contains a 3-hydroxy-3-cyclohexylpropionate unit.

TABLE 5

| | |
|---|---|
| Dry weight of the microbial cells (mg/L) | 900 |
| Weight of the polymer (mg/L) | 43 |
| Monomer unit composition (TIC peak area ratio) | |
| 3-hydroxybutyric acid | 86.1% |
| 3-hydroxydodecanoic acid | 1.4% |
| 3-hydroxy-3-cyclohexylpropionate | 12.5% |

EXAMPLE 6

*Pseudomonas cichorii* strain YN2 was inoculated in an M9 medium (200 ml) containing 0.5% of yeast extract (manufactured by Difco) and 6.0 mM of 3-cyclohexylpropionic acid, and the whole was then subjected to shaking culture with 125 strokes/min. at 30° C. After 42 hours, the microbial cells were recovered by centrifugation, followed by washing with cold methanol once and drying in vacuo.

Furthermore, the dried microbial cell pellet was suspended in 20 ml of chloroform. Then, a PHA was extracted by agitating the suspension for 185 hours at 35° C. After the extract had been filtered with a membrane filter having a pore size of 0.45 μm, the filtrate was condensed with a rotary evaporator. Then, the concentrated solution was placed in cold methanol to precipitate the PHA therein again, followed by recovering a precipitate only and drying in vacuo.

The obtained PHA was subjected to a methanolysis according to the conventional method, followed by being analyzed with a gas chromatography-mass spectrometer (GC-MS, Shimadzu QP-5050, EI method) to identify a methylesterified product of the monomer unit of the PHA. As a result, as shown in Table 5, it was confirmed that the PHA contains a 3-hydroxy-3-cyclohexylpropionate unit.

TABLE 6

| | |
|---|---|
| Dry weight of the microbial cells (mg/L) | 800 |
| Weight of the polymer (mg/L) | 24 |
| Monomer unit composition (TIC peak area ratio) | |
| 3-hydroxybutyric acid | 81.6% |
| 3-hydroxydodecanoic acid | 2.3% |
| 3-hydroxy-3-cyclohexylpropionate | 16.1% |

EXAMPLE 7

*Pseudomonas cichorii* strain YN2 was inoculated in an M9 medium (200 ml) containing 0.5% of D-glucose, 3.0 mM of 3-cyclohexylpropionic acid, and 3.0 mM of 5-cyclohexylvalerate, and the whole was then subjected to shaking culture with 125 strokes/min. at 30° C. After 40 hours, the microbial cells were recovered by centrifugation. Subsequently, the recovered cells were resuspended in an M9 medium (200 ml) containing 0.5% of D-glucose, and 3.0 mM of 3-cyclohexylpropionic acid, 3.0 mM of 5-cyclohexylvalerate in the absence of a nitrogen source (NH$_4$Cl). Then, the medium was subjected to shaking culture with 125 strokes/min. at 30° C. After 39 hours, the microbial cells were recovered by centrifugation, followed by washing with cold methanol once and drying in vacuo.

Furthermore, the dried microbial cell pellet was suspended in 20 ml of chloroform. Then, a PHA was extracted by agitating the suspension for 69 hours at 35° C. After the extract had been filtered with a membrane filter having a pore size of 0.45 μm, the filtrate was condensed with a rotary evaporator. Then, the concentrated solution was placed in cold methanol to precipitate the PHA therein again, followed by recovering a precipitate only and drying in vacuo.

The obtained PHA was subjected to a methanolysis according to the conventional method, followed by being analyzed with a gas chromatography-mass spectrometer (GC-MS, Shimadzu QP-5050, EI method) to identify a methylesterified product of the monomer unit of the PHA. As a result, as shown in Table 7, it was confirmed that the PHA contains a 3-hydroxy-3-cyclohexylpropionate unit and a 3-hydroxy-5-cyclohexylvalerate unit.

TABLE 7

| | |
|---|---|
| Dry weight of the microbial cells (mg/L) | 700 |
| Weight of the polymer (mg/L) | 520 |
| Monomer unit composition (TIC peak area ratio) | |
| 3-hydroxyoctanoic acid | 0.4% |
| 3-hydroxydecanoic acid | 0.4% |
| 3-hydroxy-3-cyclohexylpropionate | 20.9% |
| 3-hydroxy-5-cyclohexyl valerate | 78.3% |

EXAMPLE 8

*Pseudomonas cichorii* strain YN2 was inoculated in an M9 medium (200 ml) containing 0.5% of yeast extract (manufactured by Oriental Yeast, Co., Ltd.) and 6.0 mM of 3-cyclohexylpropionic acid, and the whole was then cultured at 30° C. by ventilating air with agitation, with 70 rotations/min. and an air amount of 9.4 L/min. After 40 hours, the microbial cells were recovered by centrifugation, followed by washing with cold methanol twice and drying in vacuo, resulting in a frozen dried pellet.

Furthermore, the dried microbial cell pellet was suspended in 200 ml of chloroform. Then, a PHA was extracted by agitating the suspension for 100 hours at 35° C. After the extract had been filtered with a membrane filter having a pore size of 0.45 μm, the filtrate was condensed with a rotary evaporator. Then, the concentrated solution was reprecipitated in cold methanol, followed by recovering a precipitate and drying in vacuo, to thereby yield a PHA. The resultant PHA was analyzed for monomer unit composition (TIC peak area ratio) in accordance with the method described below.

As a result, 18% of the monomer unit composition was a 3-hydroxy-3-cyclohexylpropionate unit, 81% thereof was a 3-hydroxybutyrate unit, and 1% thereof was a 3-hydroxyalkanoate unit of a medium-channel-length (MCL).

For removing the poly-3-hydroxybutyrate (PHB) component being contaminated from the PHA, the following purification procedures were performed. That is, the PHA was suspended in acetone and was then extracted for 24 hours at 60° C. Then, a supernatant was recovered by centrifugation, and a precipitated portion was extracted again with acetone. This operation was repeated five times, and also the respective supernatants were collected and were then evaporated to dryness with an evaporator. The dried sample was dissolved in a small amount of chloroform, and was then reprecipitated in cold methanol. This operation was repeated three times, and the product was then dried under reduced pressure, resulting in a PHA. The obtained PHA was analyzed for monomer unit composition (TIC peak area ratio) by the method described below. As a result, 94% of the monomer unit composition was a 3-hydroxy-3-cyclohexyl-propionate unit, and 6% thereof was a medium-chain-length 3-hydroxyalkanoate unit.

Furthermore, the PHA was evaluated for the molecular weight using gel permeation chromatography (GPC; Tosoh HLC-8020, column; Polymer Laboratory PLgel MIXED-C (5 μm), solvent; chloroform, in polystyrene equivalent). As a result, Mn=63,000 and Mw=110,000.

This PHA was designated as PHA 1 and was used as a binder resin.

Furthermore, the PHA was analyzed for monomer unit composition as follows. That is, about 10 mg of the PHA was placed in an eggplant-shaped flask (25 ml in volume) and was dissolved in 2 ml of chloroform, and furthermore 2 ml of a methanol solution containing 3% sulfuric acid was added to the flask. Subsequently, the mixture was refluxed at 100° C., while allowing a reaction for 3.5 hours. After the completion of the reaction, 10 ml of deionized water was added to the flask and the flask was shaken for 10 minutes. Thus, the mixture was separated into two layers. Then, a chloroform layer as a lower layer was removed and was then dehydrated with magnesium sulfate. The chloroform layer was put in a gas chromatography-mass spectrometer (GS-MS, Shimadzu QP-5050, column: DB-WAX (J & W, Co., Ltd. 0.32 mm×30 m), EI method) to identify the methylesterified product of the PHA monomer unit.

EXAMPLE 9

150 g of a polylactic acid (trade name: Lacty, manufactured by Shimadzu Corporation, melt viscosity: 200,000 poise at 195° C., weight average molecular weight: 200,000) and 50 g of PHA 1 of Example 8 were blended together. Then, the mixture was introduced into an injection-molding machine and was then melt-kneaded at a temperature of 195 to 230° C. to mold the product.

The resulting polymer blend was designated as PHA 2 and was then used as a binder resin.

EXAMPLE 10

100 parts by mass of PHA1 (Example 8), 5 parts by mass of magenta pigment (C.I. Pigment Red 114), and 2 parts by mass of charge control agent (NXVP434, manufactured by Hoechst Japan Ltd.)

The above components were mixed together and then melt-kneaded with a twin screw extruder (L/D=30). The kneaded product was cooled and then roughly pulverized with a hammer mill. Subsequently, the roughly pulverized product is finely pulverized with a jet mill, followed by classifying the resulting powders. As a result of the pulverization, magenta color particles 1 were obtained. The weight average particle size and fine powder quantity of the magenta color particles 1 were measured. The results thereof are listed in Table 8.

As a flow-improving agent, 1.5 parts by mass of hydrophobic silica fine powders (BET: 250 $m^2/g$) treated with hexamethyldisilazane was dry-mixed with 100 parts by mass of the magenta color particles 1 in Henschel mixer, resulting in a magenta toner 1 of this example. Furthermore, 7 parts by mass of the obtained magenta toner 1 and 93 parts by mass of a resin-coated magnetic ferrite carrier (average particle size: 45 μm) were mixed together to prepare a two-component magenta developer 1 for magnetic brush development.

For the resulting two-component magenta developer 1, using the measuring method for the charging quantity, the charging quantity of the toner described above was measured after agitating 10 seconds and 300 seconds under each of environmental conditions of:

normal temperature and normal humidity (25° C., 60% RH); and high temperature and high humidity (30° C., 80% RH).

Then, each of the measured values of the two-component blow off charging quantity was rounded to one decimal place. Then, each value was evaluated based on the following criteria. The results thereof are listed in Table 8.

⊚: Excellent (−20 μC/g or less),

O: Good (−19.9 to −10.0 μC/g),

Δ: Practicable (−9.9 to −5.0 μC/g), and

X: Impracticable (−4.9 μC/g or more).

EXAMPLE 11

A magenta toner 2 was prepared by the same way as that of Example 10, except for the use of PHA 2 instead of PHA 1. In addition, by the same method as that of Example 10, a two-component magenta developer 2 was obtained by using the magenta toner 2. The characteristics of the toner and the developer were measured by the same way as that of Example 10. The results are shown in Table 8.

COMPARATIVE EXAMPLE 1

A magenta toner 3 was prepared by the same way as that of Example 10, except that 100 parts by mass of a styrene-butylacrylate copolymer resin (glass transition temperature 70° C.) was used instead of PHA 1. In addition, by the same method as that of Example 10, a two-component magenta developer 3 was obtained by using the magenta toner 3. The characteristics of the toner and the developer were measured by the same way as that of Example 10. The results are shown in Table 8.

TABLE 8

Electrostatic properties of magenta toners 1 to 3

| | | | Particle size distribution | | Electrostatic properties | | | |
|---|---|---|---|---|---|---|---|---|
| | | | | | Normal temperature and normal humidity (Q/M) | | High temperature and high humidity (Q/M) | |
| | Number of PHA | Number of toner | Weight average particle size (μm) | Fine powder quantity (number %) | 10-second agitation | 300-second agitation | 10-second agitation | 300-second agitation |
| Example 10 | PHA 1 | Magenta 1 | 7.2 | 5.1 | ⊚ | ⊚ | ⊚ | ⊚ |
| Example 11 | PHA 2 | Magenta 2 | 6.8 | 5.2 | ⊚ | ⊚ | ⊚ | ⊚ |
| Comparative Example 1 | — | Magenta 3 | 7.0 | 4.9 | ⊚ | ⊚ | ⊚ | ⊚ |

EXAMPLE 12

A black toner 1 was prepared by the same way as that of Example 10, except that carbon black (DBP oil absorption amount 110 mL/100 g) was used instead of the magenta pigment. In addition, by the same way as that of Example 10, a two-component black developer 1 was obtained by using the black toner 1. The characteristics of the toner and the developer were measured by the same way as that of Example 10. The results are shown in Table 9.

EXAMPLE 13

A black toner 2 was prepared by the same way as that of Example 10, except that PHA 2 was used instead of PHA 1, and that carbon black (DBP oil absorption amount 110 mL/100 g) was used instead of the magenta pigment. In addition, by the same way as that of Example 10, a two-component black developer 2 was obtained by using the black toner 2. The characteristics of the toner and the developer were measured by the same way as that of Example 10. The results are shown in Table 9.

COMPARATIVE EXAMPLE 2

A black toner 3 was prepared by the same way as that of Example 10, except that 100 parts by mass of a styrene-butylacrylate copolymer resin (glass transition temperature 70° C.) was used instead of PHA 1, and carbon black (DBP oil absorption amount 110 mL/100 g) was used instead of the magenta pigment. In addition, by the same way as that of Example 10, a two-component black developer 3 was obtained by using the black toner 3. The characteristics of the toner and the developer were measured by the same way as that of Example 10. The results are shown in Table 9.

TABLE 9

Electrostatic properties of black toners 1 to 3

| | | | Particle size distribution | | Electrostatic properties | | | |
|---|---|---|---|---|---|---|---|---|
| | | | | | Normal temperature and normal humidity (Q/M) | | High temperature and high humidity (Q/M) | |
| | Number of PHA | Number of toner | Weight average particle size (μm) | Fine powder quantity (number %) | 10-second agitation | 300-second agitation | 10-second agitation | 300-second agitation |
| Example 12 | PHA 1 | Black 1 | 7.3 | 5.4 | ⊚ | ⊚ | ⊚ | ⊚ |
| Example 13 | PHA 2 | Black 2 | 7.1 | 5.6 | ⊚ | ⊚ | ⊚ | ⊚ |
| Comparative Example 2 | — | Black 3 | 7.1 | 5.1 | ⊚ | ⊚ | ⊚ | ⊚ |

EXAMPLE 14

Deinking Test

Using black toners 1 to 3 obtained in Examples 12 and 13 and Comparative Example 2, a test image having a black and white ratio of 6% was formed on the surface of paper (a basic weight of 75 g/m$^2$) to prepare test paper. Using the test paper, a paper sheet for evaluation was prepared under the following conditions:

(1) Disaggregation: An aqueous dispersion having the following composition is agitated in a beaker at 50° C. for 20 minutes to allow disaggregation.

Test paper 5.0%,
NaOH 0.7%,
Sodium silicate 3.0%,
$H_2O_2$ 1.0%, and
Deinking agent ("LIPTOL S2800", manufactured by Lion Corporation) 0.2%.

(2) Dilution, dehydration, and kneading: The aqueous dispersion is diluted with water to 5% and is then dehydrated by centrifugation. Then, pulp, sodium silicate, and so on are added to the dehydrated product, such that the resulting product could contain 20% pulp, 3.0% sodium silicate, and 0.5% NaOH, followed by dehydration with a kneader.

(3) Maturing: The kneader-disaggregated product is matured at 50° C. for 2 hours.

(4) Floatation: A dispersion of 1% pulp concentration is prepared by adding water to the matured product, and minute air bubbles are discharged into the dispersion for 7 minutes to allow the toner in the dispersion to adsorb these bubbles. As a result, the toner comes to the surface of the dispersion, so that the toner and the water can be separated from each other.

(5) Washing: 2.4 g of deinked pulp is washed twice with one litter of water for each time. Preparation of test paper sheet: A paper sheet (a basis weight of 100 g/m$^2$) is prepared using a tapping sheet machine.

(6) Evaluation of deinking performance: The number of toners on the 9 cm$^2$ of the paper sheet is observed through one's eyes and through a microscope. Then, the toners are grouped into one having a size of 100 μm or more (visually recognizable size) and the other having a size of 60 to 100 μm, followed by evaluating each of these groups.

The test results are listed in Table 10. In the table, the numerical value in the table expresses the number of residual toners.

TABLE 10

| | Result of deinking test | | |
|---|---|---|---|
| Number of toner | 60 to 100 μm (Number) | Over 100 μm (Number) | Total (Number) |
| Black 1 | 14 | 16 | 30 |
| Black 2 | 20 | 18 | 38 |
| Black 3 | 43 | 38 | 81 |

EXAMPLE 15

Biodegradability Test

Each of magenta toners 1 to 3 and black toners 1 to 3 obtained in Examples 10 to 13 and Comparative Examples 1 and 2 was molten and molded into a film shape having a thickness of about 50 μm, and was then left for six months in soil. As a result, the shapes of the respective films of magenta toner 1 and black toner 1 completely disappeared. Also, the shapes of the respective films of magenta toner 2 and black toner 2 almost disappeared. On the other hand, the shapes of the films of magenta toner 3 and black toner 3 remained.

EXAMPLES 16 TO 19 AND COMPARATIVE EXAMPLES 3 AND 4

Figure 4:
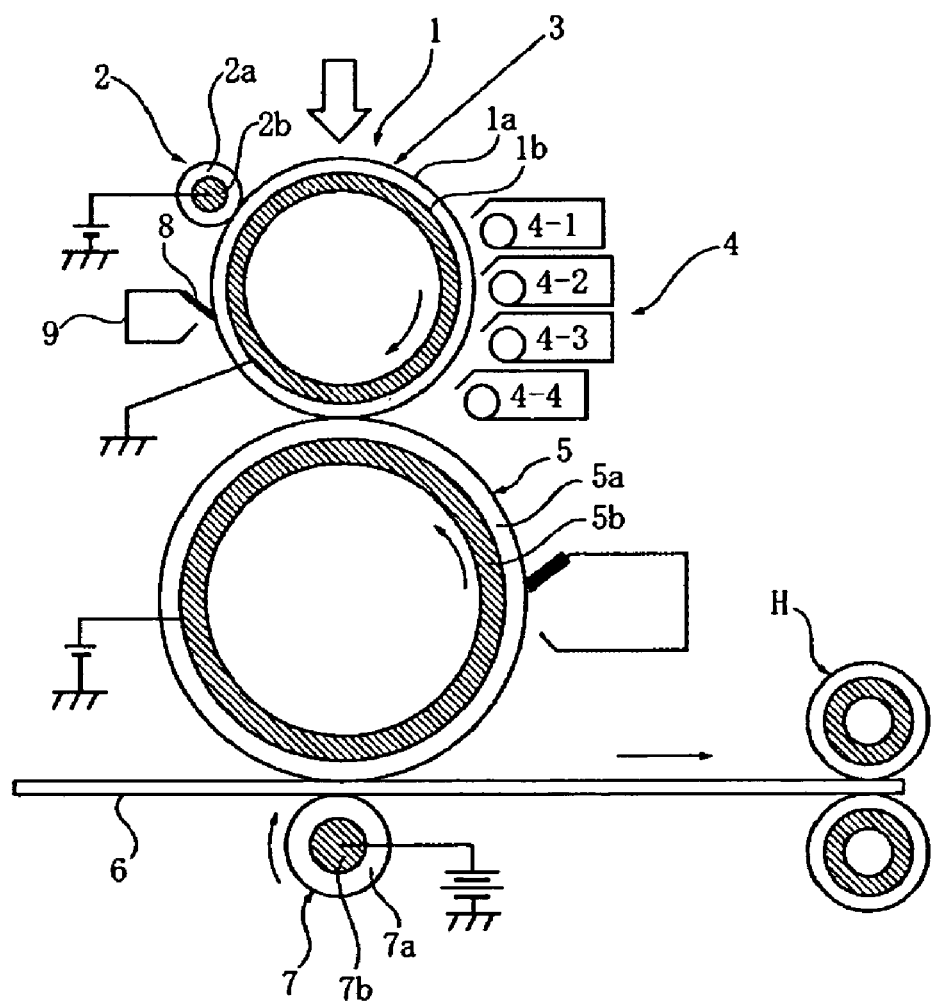
FIG. 4 is a schematic explanation view of an image-forming apparatus used in each of Examples 16 to 19 and Comparative Examples 3 and 4.

At first, an image-forming apparatus adopted in the image-forming process of each of Examples 16 to 19 and Comparative Examples 3 and 4 will be described. FIG. 4 is a schematic explanation view of the cross section of an image-forming apparatus for carrying out the image-forming process of each of the examples of the present invention and the comparative examples. A photosensitive drum 1 shown in FIG. 4 includes a photosensitive layer 1a having an organic optical semiconductor on a substrate 1b and was designed to rotate in the direction of the arrow. The charging roller 2 was a charging member facing to the photosensitive drum 1 and was brought into contact with the photosensitive drum 1 so as to rotate together. Thus, the surface of the photosensitive drum 1 was charged at a surface potential of about −600 V by the charging roller 2. As shown in FIG. 4, the charging roller 2 was constructed of a cored bar 2b covered with a conductive elastic layer 2a.

Next, the photosensitive drum 1 having the charged surface was exposed to a light 3. At this time, the light exposure was switched on and off by a polygon mirror in accordance with the information of a digital image, so that an electrostatic charge image can be formed on the photosensitive drum 1 with an exposure portion potential of −100 V and a dark portion potential of −600 V. Subsequently, the electrostatic charge image on the photosensitive drum 1 was visualized by a reversal development using a plurality of developing devices 4-1, 4-2, 4-3, and 4-4 to form a toner image on the photosensitive drum 1. At this time, a developer may be a two-component developer prepared in each of Examples 10 to 13 and Comparative Examples 1 and 2 and the toner image was formed using a magenta toner or a black toner. Then, the toner image on the photosensitive drum 1 was transferred to an intermediate transferring body 5 rotating in contact with the photosensitive drum 1. As a result, on the intermediate transferring body 5, a visualized image with four toner colors being superimposed was formed. The transfer residual toner remaining on the drum 1 was recovered in a residual toner container 9 by a cleaner member 8.

The intermediate transferring body 5 was constructed of the cored bar 5b provided as a support member and the elastic layer 5a laminated thereon as shown in FIG. 4. The intermediate transferring body 5 used in this was example was one prepared such that the elastic layer 5b was prepared by sufficiently dispersing a conductivity-imparting material (carbon black) in a nitrile-butadiene rubber (NBR) and the pipe-shaped cored bar 5b was coated with the elastic layer 5b. The hardness of the elastic layer 5b was 30 degrees, which was measured on the basis of Japanese Industrial Standard (JIS) K-6301. In addition, the volume resistivity of the elastic layer 5b was $10^9$ Ω·cm. A transferring current required for transferring the image from the photosensitive drum 1 to the intermediate transferring body 5 was about 5 μA, which was obtained by applying +500 V on the cored bar 5b from a power supply.

The visualized image of four color toners being superimposed, which was formed on the intermediate transferring body 5, was transferred to a material to be transferred 6 such as paper by the transferring roller 7, followed by being fixed and stabilized by a thermal fixing device H. The transferring roller 7 was constructed of a cored bar 7b having an outer diameter of 10 mm coated with an elastic layer 7a, in which the elastic layer 7a was prepared by providing carbon as a conductivity-imparting material and dispersing the carbon sufficiently in a foam of an ethylene-propylene-diene three dimensional copolymer (EPDM), and applying the resulting mixture thereto. The elastic layer 7a used in the present example was one having a volume resistivity of $10^6$ Ω·cm and a measured hardness of 35 degrees on the basis of JIS K-6301. In addition, a voltage was applied onto the transferring roller 7 so that the transferring current of 15 μA was allowed to flow therethrough.

Figure 7:
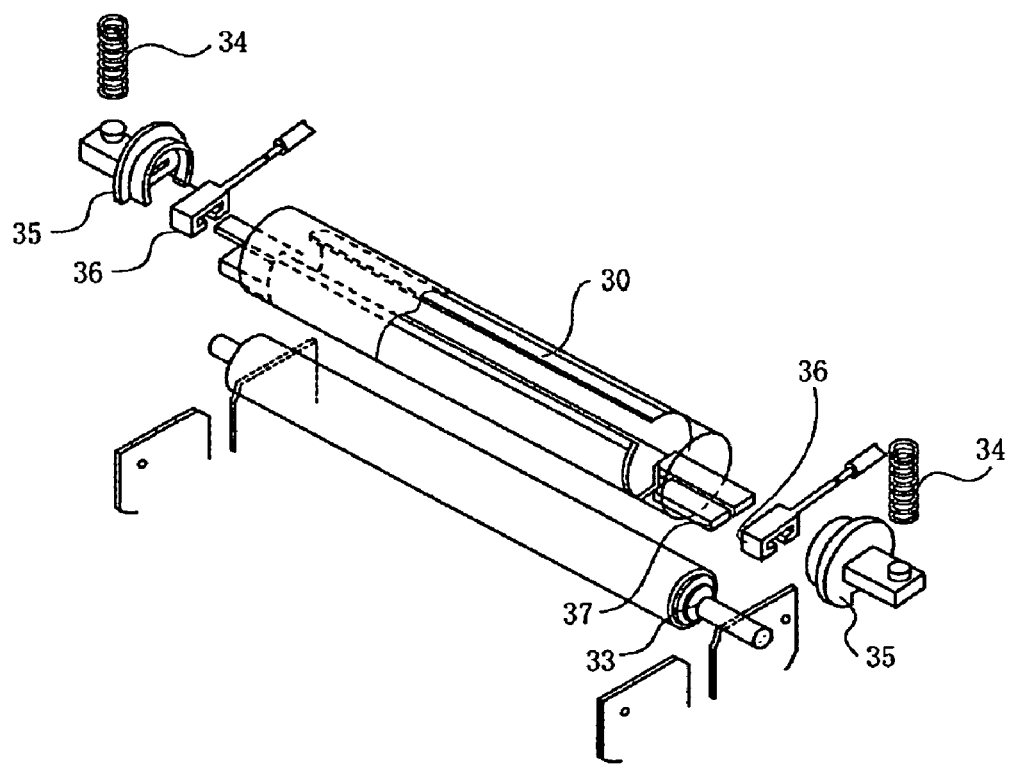
FIG. 7 is an exploded perspective view showing a main portion of a fixing device used in the examples of the present invention.
Figure 8:
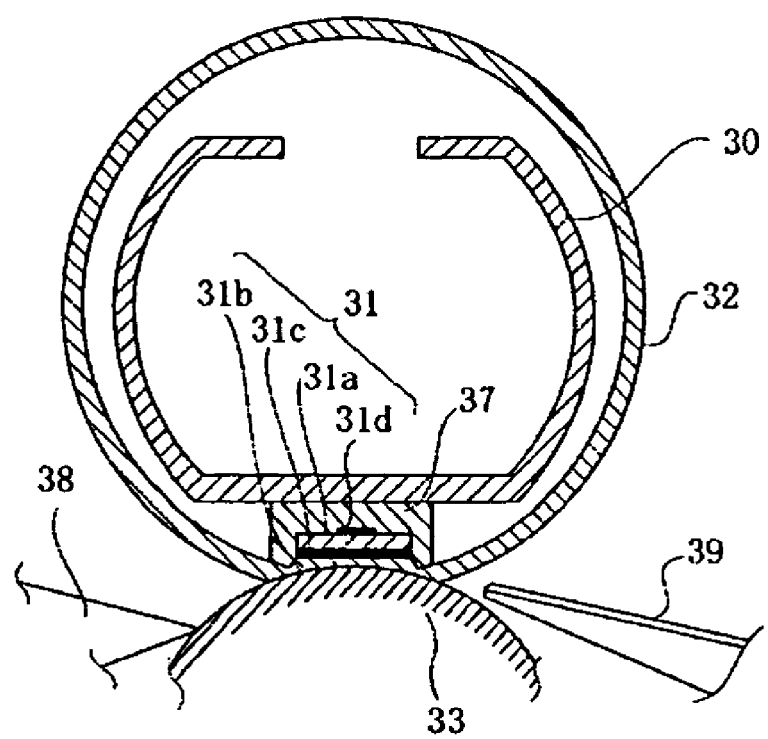
FIG. 8 is an enlarged cross-sectional diagram showing the main portion of the fixing device used in the examples of the present invention, where a state of a film at the time of suspending the fixing device.

In the apparatus shown in FIG. 4, the thermal fixing device H used was a fixing device of a heat roller type without using an oil-applying mechanism as shown in FIGS. 7 and 8. Each of upper and lower rollers used in this case was one having a surface layer made of a fluorine resin and the diameter of the roller was 60 nm. The fixing temperature at the time of fixing was set to 160° C. and a nip width was set to 7 mm. Furthermore, the transfer residual toner on the photosensitive drum 1 was recovered by cleaning and was then transported to the developing device by the reusing mechanism, followed by being reused.

Under the above conditions, the print-out test was performed as follows:

Two-component developers prepared using the toners of Examples 10 to 13 and two-component developers prepared using the toners of Comparative Examples 1 and 2 were used at a print-out speed of 8 sheets (A4-size)/minute under the conditions of normal temperature and humidity (25° C., 60% RH) or high temperature and humidity (30° C., 80% RH), respectively. In addition, the print-out test was performed with a single-color intermittent mode (i.e., the developing device was stopped for 10 seconds every time one sheet of paper was printed out, and the degradation of toner was promoted by a preliminary operation at the reboot time) while successively supplying the developer. The printed-out image was evaluated by the following items. The results of the evaluation are collectively listed in Table 11.

Evaluation of Printed-out Image (1) Image Density

A predetermined number of sheets of general plain paper for copying machines (75 g/m$^2$) were printed out and the evaluation was performed on the degree to which the image density of an image was kept at the time of terminating the printing in comparison with that of the image at an initial stage of the printing. Using the Macbeth reflection densitometer (manufactured by Macbeth Co., Ltd.), are relative density of the white background portion with an original density of 0.00 to a printed-out image was measured and used for the evaluation.

⊚: Excellent
(Image density at the end was 1.40 or more),
o: Good
(Image density at the end was 1.35 or more but less than 1.40),
Δ: Practicable
(Image density at the end was 1.00 or more but less than 1.35), and
x: Impracticable
(Image density at the end was less than 1.00).

(2) Image Fog

A predetermined number of sheets of general plain paper for copying machines (75 g/m$^2$) were printed out and the evaluation was performed on a white-solid image at the time of terminating the printing. Specifically, the evaluation was performed as follows:

The lowest value of the reflection density of the white background after the printing which was measured by using are reflectometer (REFLECTOMETER ODELTC-6DS, manufactured by TOKYO DENSHOKU CO., LTD) was defined as Ds. In addition, are reflection density average value of the sheet before the printing was defined as Dr. From these values, (Ds−Dr) was calculated and defined as the amount of fogging. Then, the amount of fogging was evaluated on the basis of the following criteria.

⊚: Excellent
(The amount of fogging was 0% or more but less than 1.5%),
o: Good
(The amount of fogging was 1.5% or more but less than 3.0%),
Δ: Practicable
(The amount of fogging was 3.0% or more but less than 5.0%), and
x: Impracticable
(The amount of fogging was 5.0% or more).

(3) Transfer Property

A predetermined number of sheets of general paper for copying machines (75 g/m$^2$) of a black-solid image were printed out and the evaluation was performed by visually observing the amount of incomplete image at the time of terminating the printing on the basis of following criteria.

⊚: Excellent (almost no incomplete image)
o: Good (slight amount of incomplete image)
Δ: Practicable
x: Impracticable As confirmed from the visual observation on the surface scratch on each of the photosensitive drum and the intermediate transferring body at the time of printing out 5,000 sheets of the image, the state where the adherence of remaining toner occurs, and an influence of the remaining toner on the printed-out image (matching with the image-forming apparatus), in each case, the surface scratch and the adherence of remaining toner cannot be observed on each of the photosensitive drum and the intermediate transferring body. Thus, matching with the image-forming apparatus was very high.

TABLE 11

| | | Evaluation results of printed-out image | | | | | |
|---|---|---|---|---|---|---|---|
| | | Normal temperature and humidity | | | High temperature and humidity | | |
| | Two-component developer | Image density | Image fog | Transfer property | Image density | Image fog | Transfer property |
| Example 16 | Magenta 1 | ⊚ | ⊚ | ⊚ | ⊚ | ⊚ | ⊚ |
| Example 17 | Magenta 2 | ⊚ | ⊚ | ⊚ | ⊚ | ⊚ | ⊚ |
| Comparative Example 3 | Magenta 3 | ⊚ | ⊚ | ⊚ | ⊚ | ⊚ | ⊚ |
| Example 18 | Black 1 | ⊚ | ⊚ | ⊚ | ⊚ | ⊚ | ⊚ |
| Example 19 | Black 2 | ⊚ | ⊚ | ⊚ | ⊚ | ⊚ | ⊚ |
| Comparative Example 4 | Black 3 | ⊚ | ⊚ | ⊚ | ⊚ | ⊚ | ⊚ |

EXAMPLES 20 AND 21 AND COMPARATIVE EXAMPLE 5

Figure 5:
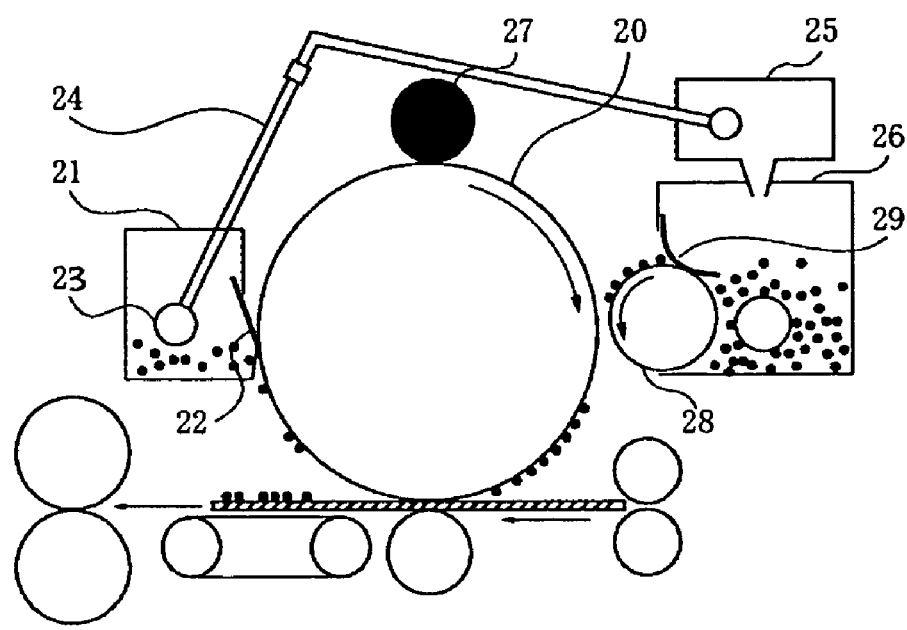
FIG. 5 is a schematic explanation view of an image-forming apparatus having a reuse mechanism of a toner used in each of Examples 20 and 21 and Comparative Example 5

For carrying out the image-forming process of each of Examples 13 and 14 and Comparative Example 5, each of the toners prepared in Examples 13 and 14 and Comparative Example 2 was used as a developer. In addition, as means for forming an image, as shown in FIG. 5, the commercially-available laser beam printer LBP-EX (manufactured by Canon Inc.) was remolded by attaching a reuse mechanism thereon to provide a reconfigured image-forming apparatus. More specifically, in the image-forming apparatus shown in FIG. 5, the untransferred toner remaining on the photosensitive drum 20 after the transfer was scrapped off by an elastic blade 22 of a cleaner 21 brought into contact with the photosensitive drum 20. Then, the toner was fed into the inside of the cleaner 21 by a cleaner roller, and was then returned to a developing device 26 through a cleaner reuse mechanism 23, via a supply pipe 24 having a conveyor screw, and a hopper 25. A system for reusing the recovered toner again was attached thereto.

In the image-forming apparatus shown in FIG. 5, the surface of the photosensitive drum 20 was charged by a first charging roller 27. The first charging roller 27 was constructed of: a rubber roller (12 mm in diameter and 50 g/cm in contact pressure) in which conductive carbon was dispersed; and a nylon resin that covers the rubber roller. On the electrostatic latent image bearing member (i.e., the photosensitive drum 20), an electrostatic latent image having a dark portion potential (VD) of −700 V and a light portion potential (VL) of −200 V was formed by a laser beam exposure (600 dpi, not shown). As a toner bearing member, there was used a developing sleeve 28 having the surface coated with a resin in which carbon black was dispersed with a surface roughness Ra of 1.1.

Figure 6:
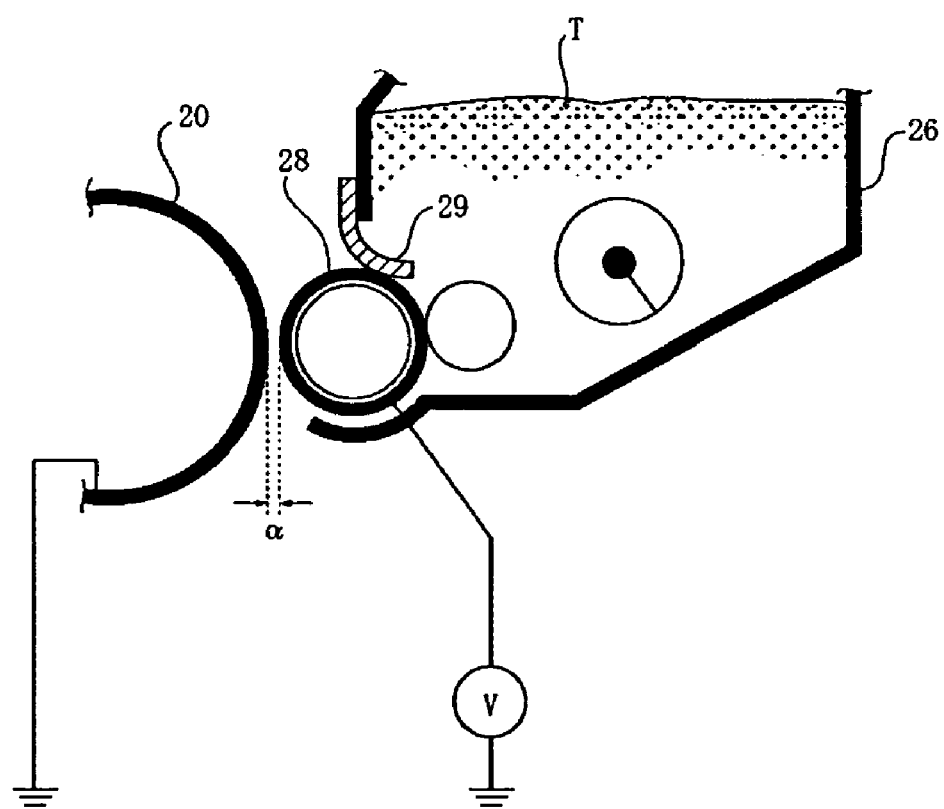
FIG. 6 is a cross-sectional view of a main portion of a developing device for a mono-component developer used in each of Examples 20 and 21 and Comparative Example 5.

FIG. 6 is an enlarged cross-sectional view of the main portion of the developing device for a mono-component developer used in each of Examples 20 and 21 and Comparative Example 5. The conditions for developing the electrostatic latent image was to set the speed of the developing sleeve 28 1.1 times higher than the moving speed of the surface of the opposing photoconductive drum 20, while the distance a between the photoconductive drum 20 and the developing sleeve 28 (S–D interspace) was set to 270 μm. As a layer thickness regulation member of the toner (T), an urethane rubber blade 29 was used so as to be brought into contact therewith. In addition, the thermal fixing device for fixing a toner image was set to 160° C. Note that the fixing device used was one shown in FIG. 7 and FIG. 8. Here, components denoted by reference numerals in the figure were as follows:

30: a stay, 31: a heating body, 31a: a heater board, 31b: a heating element, 31c: a surface protective layer, 31d: a thermometry element, 32: a fixing film, 33: a heating roller, 34: a coil spring, 35: a film-end regulation flange, 36: an electric-supply connector, 37: an insulating member, 38: an entrance guide, and 39: an exist guide (a separating guide).

As described above, 30,000 sheets were continuously printed out for the evaluation at a print-out speed of 8 sheets (A4-size)/minute under the conditions of normal temperature and normal humidity (25° C., 60% RH), while the toner was supplied in succession (i.e., the developing device was not stopped and the consumption of the toner was accelerated). The image density of each printed-out image was measured, and the running stability thereof was evaluated on the basis of the following criteria. Then, the image of 10,000th sheet was also observed and the image fog thereof was evaluated on the basis of the following criteria. Concurrently, observed was the status of each of the devices that constructed the image-forming apparatus after the running test to evaluate the matching of each device with each of the above toners. The results of the evaluation were listed in Table 12.

(1) Transition of Image Density Upon Running

A predetermined number of sheets of general plain paper for copying machines (75 g/m$^2$) were printed out and the evaluation was performed on the degree to which the image density of an image was kept at the time of terminating the printing in comparison with that of the image at an initial stage of the printing. Using the Macbeth reflection densitometer (manufactured by Macbeth Co., Ltd.), a relative density of the white background portion with an original density of 0.00 to a printed-out image was measured and used for the evaluation.

⊚: Excellent (Image density at the end was 1.40 or more), o: Good (Image density at the end was 1.35 or more but less than 1.40), Δ: Practicable (Image density at the end was 1.00 or more but less than 1.35), and x: Impracticable (Image density at the end was less than 1.00).

(2) Image Fog

A predetermined number of sheets of general plain paper for copying machines (75 g/m$^2$) were printed out and the evaluation was performed on a white-solid image at the time of terminating the printing. Specifically, the evaluation was performed as follows. The lowest value of the reflection density of the white background after the printing, which was measured by using a reflectometer (REFLECTOMETER ODELTC-6DS, manufactured by TOKYO DENSHOKU Co., LTD) was defined as Ds. In addition, a reflection density average value of the sheet before the printing was defined as Dr. From these values, (Ds−Dr) was calculated and defined as the amount of fogging. Then, the amount of fogging was evaluated on the basis of the following criteria.

⊚: Excellent (The amount of fogging was 0% or more but less than 1.5%), o: Good (The amount of fogging was 1.5% or more but less than 3.0%), Δ: Practicable (The amount of fogging was 3.0% or more but less than 5.0%), and x: Impracticable (The amount of fogging was 5.0% or more).

(3) Matching Evaluation of Image-Forming Apparatus

1. Matching with Developing Sleeve

After the completion of the printing-out test, the state of the remaining toner adhered on the surface of the developing sleeve and the influence thereof on the printed-out image were visually evaluated.

⊚: Excellent (not observed), o: Good (almost no adherence),

Δ: Practicable (some amount of toner adherence but little influence on image), and x: Impracticable (considerable degree of toner adherence and uneven image).

2. Matching With Photosensitive Drum

The degree of generation of the surface scratch, the adherence of remaining toner on the surface of the photosensitive drum, and the influence thereof on the printed-out image were visually evaluated.

⊙: Excellent
(not observed),
o: Good
(a few scratches but no influence on image),
Δ: Practicable
(some amount of toner adherence and scratch but little influence on image), and
x: Impracticable
(considerable degree of toner adherence and vertical-streak-like image defect).

3. Matching With Fixing Device

The state of the surface of the fixing film was observed. The results of evaluation on the surface property and the degree of adherence of the remaining toner were totally equalized to evaluate the durability of the toner.

(i) Surface Property
The generation of scratch, cutting, or the like on the surface of the fixing film after the completion of the printing-out test was visually observed and evaluated.
⊙: Excellent
(not observed),
o: Good
(almost no generation),
Δ: Practicable, and
x: Impracticable.

(ii) Adherence State of Remaining Toner
The state of the remaining toner being adhered on the surface of the fixing film after the completion of the printing-out test was visually observed and evaluated.
⊙: Excellent
(not observed),
o: Good
(almost no generation),
Δ: Practicable, and
x: Impracticable.

printing-out test was carried out continuously while successively supplying the black toner 1 of Example 12 (i.e., the developing device was not stopped and the consumption of the toner was accelerated). The printed-out image as well as its matching with the image-forming apparatus used was evaluated on the same items as those of each of Examples 20 and 21 and Comparative Example 5. As a result, a favorable result was obtained for each item.

What is claimed is:

1. A polyhydroxyalkanoate homopolymer comprising a monomer unit represented by the following general formula (1):

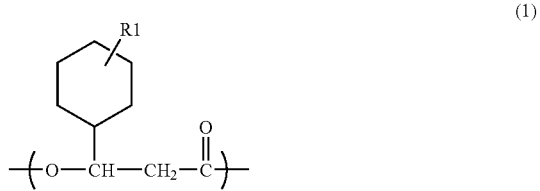

(1)

(wherein R1 represents a substituent to a cyclohexyl group, where R1 is one selected from the group consisting of a H atom, a CN group, a $NO_2$ group, a halogen atom, a $CH_3$ group, a $C_2H_5$ group, a $C_3H_7$ group, a $CF_3$ group, a $C_2F_5$ group, and a $C_3F_7$ group.

2. The polyhydroxyalkanoate homopolymer according to claim 1, wherein the monomer unit represented by the general formula (1) is a monomer unit represented by the following general formula (16):

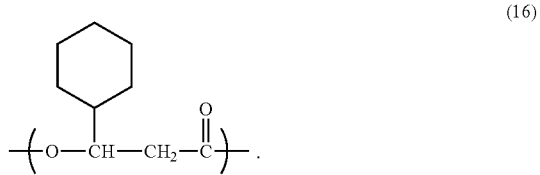

(16)

3. The polyhydroxyalkanoate homopolymer according to claim 1, wherein the polymer molecule has a number

TABLE 12

Evaluation results of printed-out image and matching with image-forming apparatus

| | | Evaluation of printed-out image | | | | | Evaluation of matching with each device | | | |
| | | Image density transition upon running | | | | Image fog at | | | Fixing device | |
| | Number of toner | Initial stage | 1,000-sheet | 10,000-sheet | 30,000-sheet | 10,000-sheet | Developing sleeve | Photosensitive drum | Surface property | Adherence of toner |
|---|---|---|---|---|---|---|---|---|---|---|
| Example 20 | Black 1 | ⊙ | ⊙ | ⊙ | ⊙ | ⊙ | ⊙ | ⊙ | ⊙ | ⊙ |
| Example 21 | Black 2 | ⊙ | ⊙ | ⊙ | ⊙ | ⊙ | ⊙ | ⊙ | ⊙ | ⊙ |
| Comparative Example 5 | Black 3 | ⊙ | ⊙ | ⊙ | ⊙ | ⊙ | ⊙ | ⊙ | ⊙ | ⊙ |

EXAMPLE 22

The toner reuse mechanism was detached from the image-forming apparatus shown in FIG. 5 and was subjected to the printing-out test similarly to the case of each of Examples 20 and 21 and Comparative Example 5, except that a printing-out speed was changed to 16 sheets (A4 size)/minute. The average molecular weight of 2,000 or more and 300,000 or less.

4. The polyhydroxyalkanoate homopolymer according to claim 1, where R1 is neither an H atom nor a halogen atom.

* * * * *